US 11,707,637 B2

United States Patent
Marquet et al.

(10) Patent No.: US 11,707,637 B2
(45) Date of Patent: *Jul. 25, 2023

(54) FOCUSED ULTRASOUND CARDIAC STIMULATION SYSTEM, PORTABLE DEVICE AND CARDIAC STIMULATION, AND ASSOCIATED METHODS

(71) Applicants: UNIVERSITE DE BORDEAUX, Bordeaux (FR); INSTITUT NATIONAL DE LA SANTE ET DE LA RECHERCHE MEDICALE, Paris (FR); CENTRE HOSPITALIER UNIVERSITAIRE DE BORDEAUX, Talence (FR)

(72) Inventors: Fabrice Marquet, Bordeaux (FR); Pierre Bour, Talence (FR); Bruno Quesson, Bordeaux (FR); Fanny Vaillant, Bordeaux (FR); Remi Dubois, Mérignac (FR)

(73) Assignees: UNIVERSITE DE BORDEAUX, Bordeaux (FR); INSTITUT NATIONAL DE LA SANTE ET DE LA RECHERCHE MEDICALE, Paris (FR); CENTRE HOSPITALIER UNIVERSITAIRE DE BORDEAUX, Talence (FR)

( * ) Notice: Subject to any disclaimer, the term of this patent is extended or adjusted under 35 U.S.C. 154(b) by 615 days.

This patent is subject to a terminal disclaimer.

(21) Appl. No.: 15/508,215

(22) PCT Filed: Sep. 1, 2015

(86) PCT No.: PCT/EP2015/069964
§ 371 (c)(1),
(2) Date: Mar. 2, 2017

(87) PCT Pub. No.: WO2016/034590
PCT Pub. Date: Mar. 10, 2016

(65) Prior Publication Data
US 2017/0281984 A1    Oct. 5, 2017

(30) Foreign Application Priority Data
Sep. 2, 2014 (FR) .................................. 1458210

(51) Int. Cl.
*A61N 7/02* (2006.01)
*G01R 33/48* (2006.01)
(Continued)

(52) U.S. Cl.
CPC .............. *A61N 7/02* (2013.01); *A61B 5/0044* (2013.01); *A61B 5/01* (2013.01); *A61B 5/055* (2013.01);
(Continued)

(58) Field of Classification Search
CPC .. A61N 7/02; A61B 17/320068; A61B 90/37; A61B 5/107; A61B 5/0044;
(Continued)

(56) References Cited

U.S. PATENT DOCUMENTS 5,526,814 A * 6/1996 Cline ................. A61B 17/2256
600/411
6,042,556 A * 3/2000 Beach ...................... A61N 7/02
600/437

(Continued)

FOREIGN PATENT DOCUMENTS

| CN | 103202727 A | 7/2013 |
| EP | 0 627 206 A2 | 12/1994 |
| WO | WO 2009/002492 A1 | 12/2008 |

OTHER PUBLICATIONS

Mougenot et al., "Three-Dimensional Spatial and Temporal Temperaturecontrol With MR Thermometry-Guided FocusedUltrasound (MRgHIFU)", Magnetic Resonance in Medicine 61:603-614 (2009) (Year: 2009).*

(Continued)

*Primary Examiner* — Luther Behringer
*Assistant Examiner* — Amy Shafqat
(74) *Attorney, Agent, or Firm* — Pillsbury Winthrop Shaw Pittman LLP

(57) ABSTRACT

An ultrasound cardiac stimulation system includes: a system for measuring the heart electrical activity; a system for generating a beam of focussed ultrasound signals focussed on a targeted zone, the signals being calibrated to generate electrical stimulation in a zone of the heart, the beam generation being synchronised with a first selected time of the electrocardiogram, the generation of the beam corre- (Continued)

sponding to a pulse with a duration of less than 80 ms; a system for locating the targeted zone coupled with a system for positioning the system for generating the focussed beam to control the beam of focussed ultrasound signals in the targeted zone, the location system being synchronised with the system for generating the beam of focussed signals; a single monitoring system following in real time a temperature and tissue deformation in the targeted zone, the monitoring system taking measurements in synchronisation with the rhythm of the electrocardiogram.

15 Claims, 8 Drawing Sheets

(51) Int. Cl.
| | |
|---|---|
| *A61B 90/00* | (2016.01) |
| *A61B 5/055* | (2006.01) |
| *A61B 5/00* | (2006.01) |
| *A61B 5/107* | (2006.01) |
| *A61B 5/01* | (2006.01) |
| *A61B 5/318* | (2021.01) |
| *A61B 17/32* | (2006.01) |
| *A61B 18/00* | (2006.01) |
| *A61B 17/00* | (2006.01) |
| *A61B 5/113* | (2006.01) |

(52) U.S. Cl.
CPC .............. *A61B 5/107* (2013.01); *A61B 5/318* (2021.01); *A61B 5/7292* (2013.01); *A61B 17/320068* (2013.01); *A61B 90/37* (2016.02); *G01R 33/4804* (2013.01); *G01R 33/4814* (2013.01); *A61B 5/113* (2013.01); *A61B 2017/00044* (2013.01); *A61B 2017/00084* (2013.01); *A61B 2017/00243* (2013.01); *A61B 2018/00351* (2013.01); *A61B 2018/00779* (2013.01); *A61B 2018/00791* (2013.01); *A61B 2018/00839* (2013.01); *A61B 2090/373* (2016.02); *A61B 2090/374* (2016.02); *A61B 2090/378* (2016.02); *A61B 2560/0223* (2013.01)

(58) Field of Classification Search
CPC ..... A61B 5/7292; A61B 5/055; A61B 5/0402; A61B 5/01; A61B 2018/00702; A61B 2018/00577; A61B 2018/00648; A61B 2090/373; A61B 2017/00243; 2017/00084; A61B 2090/378; A61B 2090/374; A61B 5/113; A61B 2560/0223; A61B 2018/00839; A61B 2018/00791; A61B 2018/00779; A61B 2018/00351; A61B 2017/00044; G01R 33/4814; G01R 33/4804

See application file for complete search history.

(56) References Cited

U.S. PATENT DOCUMENTS

| | | | |
|---|---|---|---|
| 6,508,774 B1* | 1/2003 | Acker | A61N 7/02 601/1 |
| 6,735,461 B2* | 5/2004 | Vitek | G01R 33/28 600/411 |
| 6,936,046 B2 | 8/2005 | Hissong | |
| 8,206,299 B2* | 6/2012 | Foley | A61B 8/4209 600/439 |
| 8,229,544 B2* | 7/2012 | Tseng | G01R 33/4804 600/412 |
| 9,144,693 B2* | 9/2015 | Appelman | A61N 7/02 |
| 10,406,384 B2* | 9/2019 | Kohler | G01R 33/5611 |
| 10,675,113 B2* | 6/2020 | Andrews | A61B 5/0036 |
| 2003/0117136 A1* | 6/2003 | Wang | G01R 33/5676 324/309 |
| 2004/0034301 A1 | 2/2004 | Falco | |
| 2006/0005265 A1 | 1/2006 | Bughrara et al. | |
| 2006/0052695 A1* | 3/2006 | Adam | A61N 7/00 600/437 |
| 2006/0052701 A1* | 3/2006 | Carter | A61B 8/4254 600/439 |
| 2008/0249395 A1 | 10/2008 | Shachar et al. | |
| 2008/0269607 A1 | 10/2008 | Ishida et al. | |
| 2009/0177085 A1* | 7/2009 | Maxwell | A61B 17/22004 600/439 |
| 2009/0270730 A1* | 10/2009 | Azuma | A61B 8/485 600/443 |
| 2010/0208957 A1 | 8/2010 | Chen et al. | |
| 2011/0208095 A1* | 8/2011 | Jolesz | A61N 7/00 601/2 |
| 2012/0089132 A1* | 4/2012 | Dick | A61B 5/0095 606/4 |
| 2013/0150756 A1* | 6/2013 | Vitek | A61B 8/0875 601/2 |
| 2013/0184697 A1 | 7/2013 | Han et al. | |
| 2014/0058293 A1* | 2/2014 | Hynynen | A61B 8/085 601/2 |

OTHER PUBLICATIONS

International Search Report as issued in International Patent Application No. PCT/EP2015/069964, dated Jan. 13, 2016.
Final Office Action as issued in U.S. Appl. No. 15/508,193, dated Jul. 2, 2021.
Non-Final Office Action as issued in U.S. Appl. No. 15/508,193, dated Oct. 22, 2021.
Notice of Allowance as issued in U.S. Appl. No. 15/508,193, dated Oct. 18, 2022.
Non-Final Office Action as issued in U.S. Appl. No. 15/508,193, dated Jun. 16, 2022.

* cited by examiner

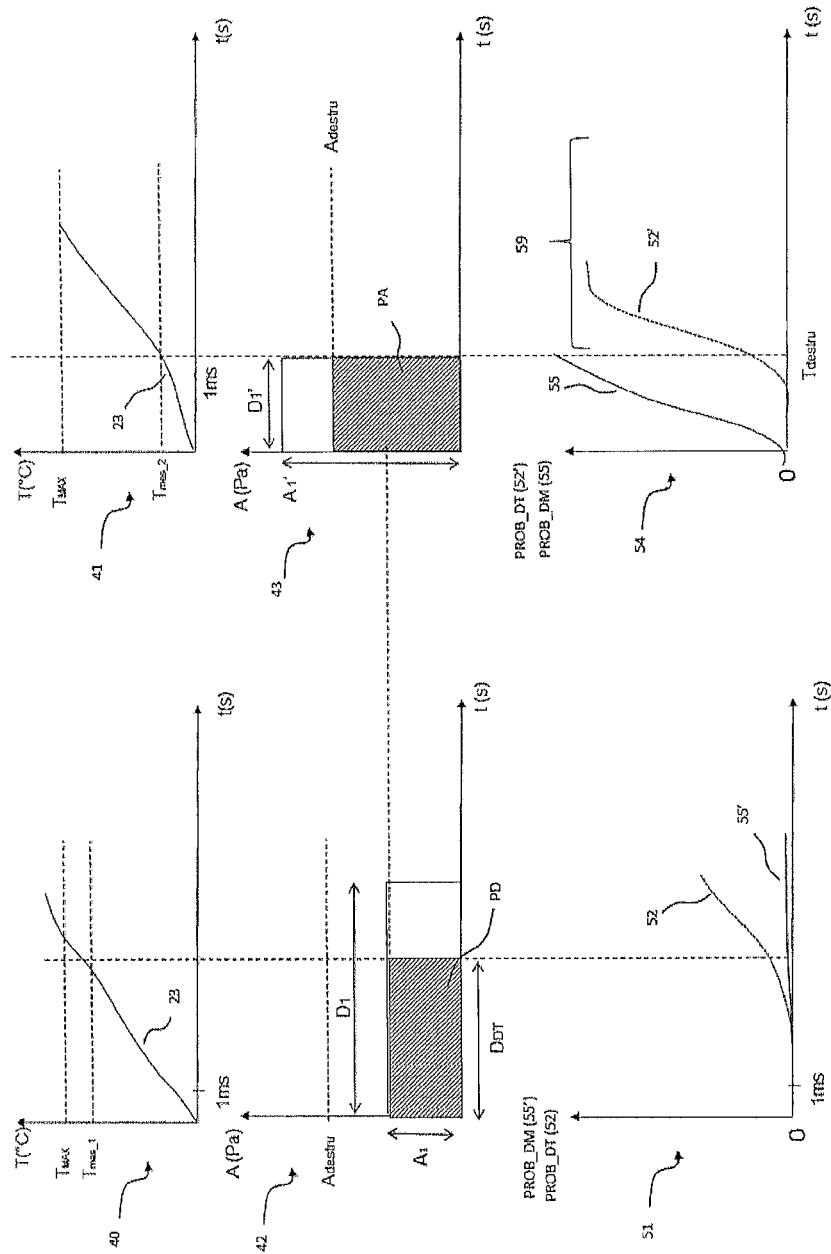

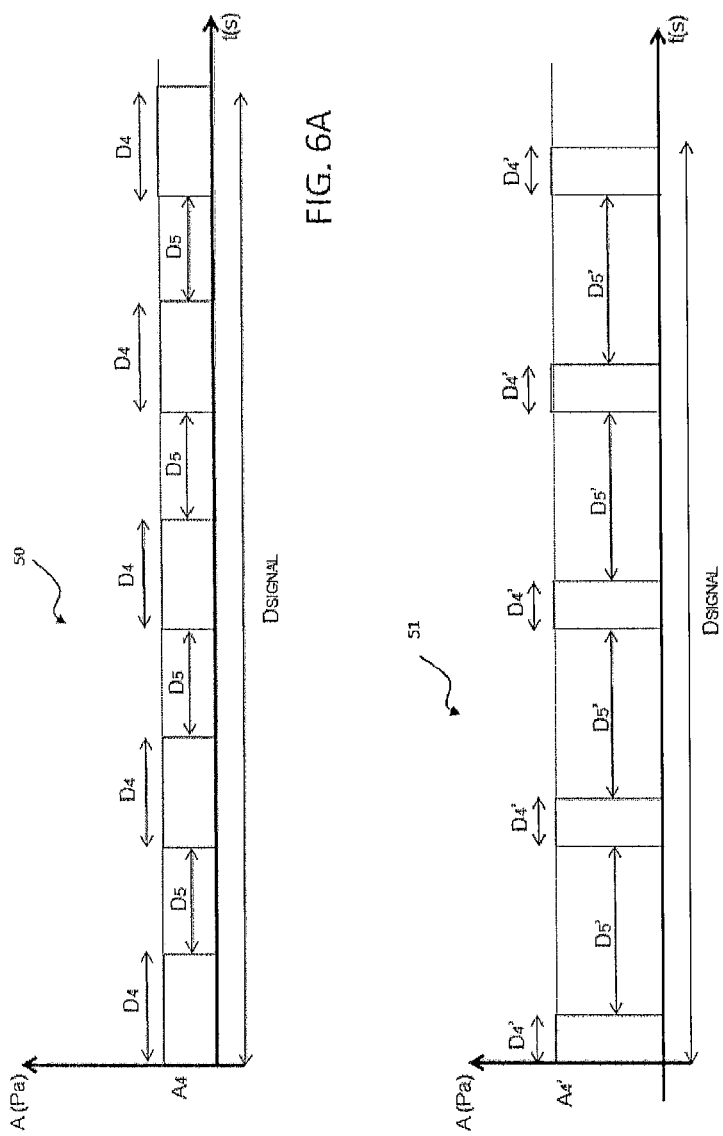

FOCUSED ULTRASOUND CARDIAC STIMULATION SYSTEM, PORTABLE DEVICE AND CARDIAC STIMULATION, AND ASSOCIATED METHODS

CROSS-REFERENCE TO RELATED APPLICATIONS

This is the U.S. National Stage of PCT/EP2015/069964, filed Sep. 1, 2015, which in turn claims priority to French Patent Application No. 1458210, filed Sep. 2, 2014, the entire contents of all applications are incorporated herein by reference in their entireties.

FIELD

The field of the invention relates to methods for calibrating a system for generating an ultrasound signal and the monitoring thereof for the stimulation of various regions of the heart. More particularly, the invention relates to a method for cardiac stimulation by means of a phased array of focussed ultrasound signals. The invention relates to different applications of the stimulation by ultrasounds of which notably the cardiac resynchronisation of the ventricles or the auricles, the generation of a ventricular or auricular fibrillation, the generation of an extrasystole, the detection of a non-responding zone of the heart, or instead an application of cardiac rhythm modification.

PRIOR ART

Today, different solutions exist making it possible to treat cardiac rhythm disorders. To treat these dysfunctions of the heart, it is known to use ultrasounds to stimulate cardiac tissue. The stimulation may be carried out by the extracorporeal generation of an ultrasound signal by means of a phased array of focussed signals.

The monitoring of the ultrasound signal generated is indispensable to determine and treat with precision the region to treat and thereby avoid any undesirable damage to the targeted or adjacent regions of the heart.

To this end, the patent US n°2006/005265 pertains to cardiac stimulation by ultrasounds controlled by the coupling of an electrocardiograph measuring the electrical activity of the heart with an imaging system. This patent application notably evokes an ultrasound imaging system making it possible to locate the responses to the stimulation at several points of the heart.

This solution makes it possible to adjust the stimulation of the heart. The intensity of the ultrasound signal is notably controlled by the generation of an ultrasound signal, firstly of low power, then increasing it little by little to avoid any deterioration of the tissues.

A drawback of this method is that it does not make it possible to quantify the thermal and mechanical damage caused by the stimulation.

Furthermore, another problem of solutions known from the prior art is that they do not make it possible to generate configurations of ultrasound signals which can create a cardiac stimulation without generating thermal damage in a targeted zone.

SUMMARY OF THE INVENTION

The invention aims to overcome the aforementioned drawbacks. Notably, the invention makes it possible to measure or anticipate mechanical and thermal damage of cardiac tissues after exposure of a zone of the heart to a phased array of ultrasound focussed signals or a generator of ultrasound signals. A particularity of an embodiment of the invention is monitoring the temperature and/or its variations in a zone substantially merged with or close to the focussed zone to prevent damage to tissues.

A subject matter of the invention relates to a method for monitoring a zone of the heart. The method comprises:
  an acquisition of the rhythm of the electrocardiogram of the heart;
  an acquisition of at least one image of a region of the heart in which a targeted zone is located, said at least one image being acquired in synchronisation with the rhythm of the electrocardiogram of the heart by an imaging system;
  a generation of a first beam of focussed ultrasound signals in the targeted zone, said beams being emitted by a phased array, said signals being configured in phase to generate at least one pulse in a focussed zone, said at least one pulse being synchronised with the rhythm of the electrocardiogram (ECG) of the heart, the pulse having a predefined amplitude and duration;
  a determination of a temperature of the focussed zone from an acquisition of at least one image by means of an imaging system;
  a determination of tissue deformation in the focussed zone in response to at least one pulse of the first focussed beam.

According to another embodiment, the invention comprises a step of determining a level of cavitation in the focussed zone in response to at least one pulse of the first focussed beam. This step may be carried out alternatively to the step of determining tissue deformation indicated beforehand. Moreover, this step may also be conducted jointly with the determination of tissue deformation. In the latter case, the two measurements may be corroborated to qualify the stimulated zone.

An advantage of such a method is to carry out a monitoring of certain parameters such as temperature, tissue deformation and/or electrical activity and/or the level of cavitation in the targeted zone in order to calibrate the beam of ultrasound signals while generating the suitable amplitude and duration during the cardiac stimulation.

An advantage of an embodiment of the process of the invention is the use of an MRI imaging device making it possible to obtain information on temperature and information on the displacement of tissues linked to the ultrasound thrust. The process of the invention thus makes it possible, with a single item of equipment, to carry out visual monitoring of any damage and to control the phased array of focussed signals.

According to another embodiment, an imaging system such as an echograph system makes it possible to obtain temperature information at the level of the focussed zone and in zones neighbouring the focussed zone.

According to an embodiment, the monitoring method comprises:
  a determination of an electrical activity in the focussed zone in response to at least one pulse, said at least one pulse having a duration less than or equal to 1 ms.

According to an embodiment, the monitoring method comprises:
  a dynamic control of the position of the focussed zone on the position of the targeted zone by means of a positioning system making it possible to measure respiratory movements of the heart in a reference frame linked to the phased array and to deduce therefrom a compensation parameter to calculate a new position of the targeted zone, said phased array automatically applying a phase parameter to each signal to deflect the beam to the new position of the targeted zone.

According to an embodiment, the monitoring method comprises:
- a determination by an imaging system of the image of the transcostal wall projected in an image plane of the phased array by taking into consideration the position and the orientation of the phased array;
- an activation or a deactivation of each element of the phased array in accordance with the position of said elements with regard to the position of the projected image of the transcostal wall.

According to an embodiment, the monitoring method comprises:
- a dynamic control of the deactivation and the activation of the elements of the phased array as a function of the calculation of each phase parameter applied to each of the signals.

According to an embodiment, the temperature in the focussed zone and tissue deformation are determined by a single imaging system, said imaging system being an MRI imaging system, the data acquired by the MRI imaging system making it possible to deduce local deformation of the tissue induced by the ultrasound pressure generated by the beam of ultrasound signals and a local rise in temperature induced by the energy generated locally by the beam of ultrasound signals.

According to an embodiment, a comparison of the position of the focussed zone determined by an imaging system and the position of the targeted zone determined by the positioning system generates at least one data for calibrating elements of the phased array so as to make a position of the focussed zone correspond with the position of the targeted zone.

According to an embodiment, the positioning system may be notably:
- either an MRI imaging system, the positions being calculated from imaging processing;
- or a positioning system comprising at least one emitter emitting ultrasound waves and a plurality of ultrasound sensors detecting the reflected waves, the positions being determined by triangulation.

This positioning system is advantageously used for the monitoring process and the stimulation process.

According to an embodiment, the monitoring method comprises a measurement of the electrical activity generated by the electrical depolarisation induced by the application of at least one ultrasound pulse in the targeted zone.

According to an embodiment, the monitoring method comprises a calibration of a signal generated in the focussed zone by the definition of parameters comprising at least one level of the amplitude and duration of a pulse as a function of at least one data among which:
- a temperature set point in the focussed zone and/or in neighbouring zones and/or in the ribs of the transcostal wall, and/or
- a tissue deformation set point in the focussed zone, and/or
- a level of cavitation set point in the focussed zone, and/or
- a detection of movement of the focussed zone in a reference point linked to the phased array, and/or
- an electrical activity set point in the focussed zone.

According to an embodiment, the electrical activity generated by the focussed beam ($F_{US}$) and measured in or near to the targeted zone is correlated with the measurements of tissue deformations in the same targeted zone obtained by the imaging system, said correlation making it possible to determine an indicator of mechanical-electrical activity of the cardiac tissue of a given targeted zone.

According to an embodiment, the generation of a first beam of focussed ultrasound signals in the targeted zone is engaged such that the at least one pulse is generated during repolarization of the cardiac tissues in the targeted zone.

According to an embodiment, the method comprises a calibration of a first focussed signal comprising a plurality of pulses, each pulse having a first duration, an amplitude, said signal being applied for a duration in a targeted zone.

According to an embodiment, the monitoring method is carried out in different targeted zones of the heart, the method further comprising, after the application of a beam of focussed signals:
- a reading of different values representing either tissue deformations of each targeted zone, or electrical levels measured near to or in each targeted zone;
- a reading of the times of electrical responses or deformations of each targeted zone;
- a calibration of signals for each targeted zone, said signals being configured with each other with a time delay dependent on the response time readings.

According to an embodiment, at least one targeted zone of the heart is indicated as "non-responding" when the tissue deformation or the electrical activity or the level of cavitation in this zone is less than a predetermined threshold for a given amplitude and duration of at least one pulse of the focussed beam and a given temperature in the focussed zone.

The process of the invention also relates to a cardiac stimulation method, also called electrical stimulation method. The electrical stimulation method may advantageously comprise the characteristics defining the embodiments of the monitoring method. In particular, the items of equipment used for the two methods may be identical and the measured parameters and the configurations may be similar.

The method for cardiac stimulation of a given zone of a heart by generation of a beam of focussed ultrasound signals comprises:
- an acquisition of the rhythm of the electrocardiogram of the heart;
- a determination of at least one position of a targeted zone in the heart;
- a generation of a beam of focussed ultrasound signals and synchronised with the rhythm of the electrocardiogram of which:
  - an amplitude of the pulses is configured such that the acoustic pressure applied in the focussed zone is comprised in a first range of pressures of [2-12 MPa];
  - a duration of the pulses is comprised in a first range of durations of [50 μs-50 ms];
  - the duration of application of the focussed beam being above 50 μs,
- a control of the position of the focal zone of the beam on the position of the targeted zone calculated in real time by means of a positioning system;
- an active monitoring in real time:
  - of a temperature in the focussed zone from an acquisition of image(s) not exceeding a predetermined threshold;
  - of a tissue deformation after each pulse comprised in a predefined range of values from an imaging system and/or of an electrical activity and/or of a level of cavitation in the focussed zone measured after each pulse comprised in a range of predefined values;

of a synchronisation parameter ensuring the respect of the synchronisation of the rhythm of the electrocardiogram with the rhythm of the pulses of the focussed beam.

In particular the process of the invention comprises two modes of generating signals which are grouped together according to ranges of values and for which thermal and mechanical damage may be monitored in real time or anticipated by a pre-configuration.

According to an embodiment, the temperature in the focussed zone $Z_F$ and tissue deformation are determined by a single imaging system, said imaging system being, for example, an MRI imaging system.

According to a first alternative embodiment, the amplitude of the pulses is configured such that the acoustic pressure applied in the focussed zone is comprised in a second range of pressures of [2-8 MPa] for pulse durations comprised in a second range of durations [1 ms-50 ms], said generated pulses causing an electrical stimulation while maintaining a threshold of mechanical deformation of the cardiac tissue less than a threshold value, said threshold value being calculated from a parameter corresponding to a given proportion of a contraction or a relaxation or an elasticity of the tissue.

According to a first alternative embodiment, the amplitude of the pulses is configured such that the acoustic pressure applied in the focussed zone is comprised in a third range of pressures of [6-12 MPa] for pulse durations comprised in a third range of durations [50 µs-1 ms], said generated pulses causing an electrical stimulation in the cardiac tissues while maintaining locally in the targeted zone a temperature threshold below a threshold temperature.

According to an embodiment, a second monitoring of zones near to the focussed zone is carried out, said second monitoring including the measurement of at least one of the following parameters in real time:
  a temperature of at least one zone neighbouring the focussed zone, and/or
  a tissue deformation in at least one zone neighbouring the focussed zone in response to at least one pulse of the first focussed beam, and/or
  an electrical activity in at least one zone neighbouring the focussed zone in response to at least one pulse of the first focussed beam, and/or
  a level of cavitation in at least one zone neighbouring the focussed zone in response to at least one pulse of the first focussed beam.

According to an embodiment, the stimulation method of the invention comprises beforehand:
  a calibration of a focussed beam according to the monitoring process of the invention;
  said calibration making it possible to determine the following parameters:
    an amplitude of pulses configured such that the acoustic pressure applied in the focussed zone is comprised in the first range of pressures of [2-12 MPa];
    a duration of application of the focussed beam over a period above 50 µs.

According to an example, the duration of the pulses is comprised in a first range of durations $G_{D1}$ of [50 µs-50 ms].

According to an embodiment, the stimulation method comprises:
  a determination of the position in space of one or more targeted zone(s) by means of an analysis of a plurality of images acquired by an MRI imaging system;
  a control of the beams focussed over time on the targeted zone(s).

According to an embodiment, the stimulation method comprises:
  a determination of the position in space of the targeted zone by means of an analysis of the signals by ultrasound probes;
  a control of the beams focussed over time on the targeted zone.

According to an embodiment, the stimulation method comprises:
  a determination of the position in space of the targeted zone ($Z_C$) by means of an analysis of the signals by intracardiac catheters introduced into the heart of which a probe is positioned near to the targeted zone ($Z_C$);
  a control of the focussed beams ($F_{US}$) over time on the targeted zone ($Z_C$).

According to an embodiment, the stimulation method is applied for the resynchronisation of the auricles or the resynchronisation of the ventricles. For this purpose, the stimulation method comprises:
  an acquisition of an electrocardiogram of the heart indicating the rhythm of the electrocardiogram of the heart;
  a determination of one or more targeted zones in which the calibrated beam of ultrasound signals is generated;
  a synchronisation of each pulse of the focussed beam with the rhythm of the electrocardiogram of the heart, each pulse being generated between the end of electrical repolarisation and the start of depolarisation of a ventricle or an auricle.

According to an embodiment, the stimulation method is applied to the generation of a cardiac fibrillation. For this purpose, the stimulation method comprises:
  an acquisition of an electrocardiogram of a ventricle of the heart indicating the rhythm of the electrocardiogram of the heart;
  a determination of at least one targeted zone in which the calibrated beam of ultrasound signals is generated;
  a synchronisation of each pulse of the focussed beam over a period during which the cardiac tissues are polarised;
  an analysis of the electrical response of the targeted zone and of the ECG so as to verify the generation of a ventricular or auricular fibrillation.

According to an embodiment, the stimulation method is applied to the detection of a zone generating an extrasystole. For this purpose, the stimulation method comprises:
  an acquisition of an electrocardiogram of a heart indicating the rhythm of the electrocardiogram of the heart, said electrocardiogram including the presence of an extrasystole taking place at an identified time of the electrocardiogram;
  a determination of at least one targeted zone in which the calibrated beam of ultrasound signals is generated;
  a synchronisation of each pulse of the focussed beam with the identified time of the electrocardiogram of the heart;
  an analysis of the electrical response or the tissue deformation in such a way as to identify whether the targeted zone is generator of the extrasystole.

According to an embodiment, the stimulation method is applied to the modification of the cardiac frequency. For this purpose, the stimulation method comprises:
  an acquisition of an electrocardiogram of a heart indicating the rhythm of the electrocardiogram of the heart;
  a determination of a plurality of targeted zones in which the calibrated beam of ultrasound signals is generated;
  a generation of a beam of focussed signals of which the frequency of pulses is different to the frequency of the electrocardiogram so as to synchronise the cardiac rhythm with the pulses of the focussed beam.

Another subject matter of the invention relates to an ultrasound cardiac stimulation system comprising:
- a means for measuring the electrical activity of the heart for the acquisition of an electrocardiogram;
- a means for generating a beam of focussed ultrasound signals in a targeted zone, said signals being calibrated such as to generate an electrical stimulation in a zone of the heart, said beam generation being synchronised with a first selected time of the electrocardiogram;
- a means for locating the targeted zone coupled to a means for positioning the means for generating the focussed beam so as to control said beam of focussed ultrasound signals in the targeted zone, said location means being synchronised with the means for generating the beam of focussed signals,
- a same means of monitoring capable of following in real time a temperature and a tissue deformation in the targeted zone, said means for monitoring taking measurements in synchronisation with the rhythm of the electrocardiogram.

According to an embodiment, the positioning system and the means for monitoring the temperature are a single MRI imaging system.

The system of the invention makes it possible to implement the steps of the monitoring process and the stimulation process of the invention.

Finally, the invention relates to a portable cardiac stimulation device responding to emergency situations. The portable device may advantageously be pre-calibrated according to the monitoring process of the invention.

The portable ultrasound cardiac stimulation device is intended to be affixed in contact with the skin of a patient. It comprises an electrical system enabling a measurement of cardiac activity indicating at least the heart beat frequency, if need be a generator of ultrasound signals, a sensor of mechanical effect making it possible to measure the presence of a contraction of the heart, said portable device comprising at least one pre-configuration defining at least one pulse train of ultrasound signals synchronised with the cardiac frequency acquired by the electrical system, said device comprising a means for activating the generator of ultrasound signals.

BRIEF DESCRIPTION OF THE FIGURES

Other characteristics and advantages of the invention will become clearer on reading the detailed description that follows, with reference to the appended figures, which illustrate:

FIGS. 5A, 5B: diagrams representing the evolution of the temperature, mechanical and/or thermal damage at the level of the targeted zone according to the amplitude and the duration of the pulses of a beam of ultrasound signals in said zone;

FIG. 6A: a diagram representing the stimulation of a targeted zone of the heart for which the pulses are of small amplitudes and of long durations;

FIG. 6B: a diagram representing the stimulation of a targeted zone of the heart for which the pulses are of high amplitudes and of which the pulse durations are short;

DESCRIPTION

Definitions and Introduction of the Principle

Figure 1:
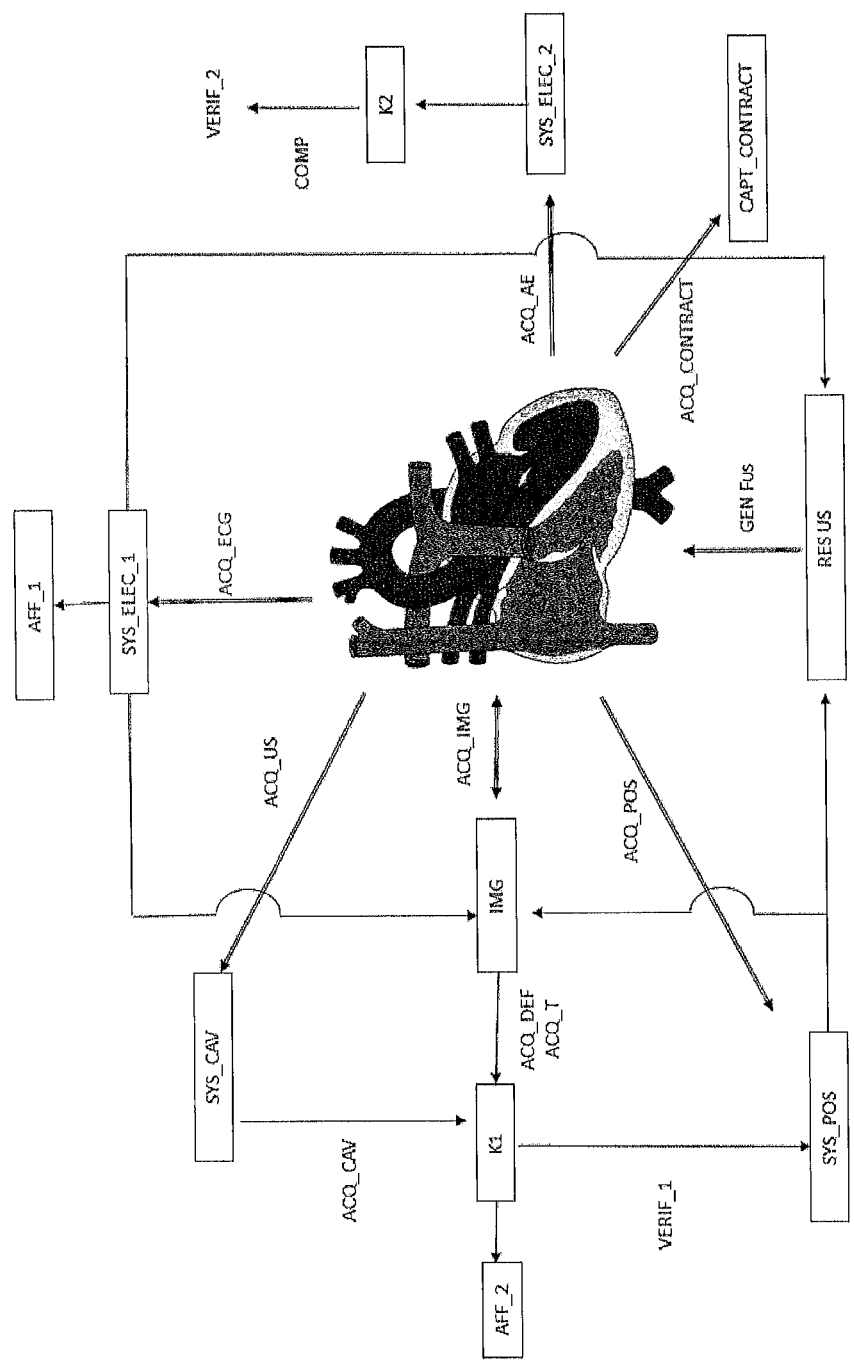
FIG. 1: a general operational diagram of the process of the invention according to an embodiment.

FIG. 1 represents a general operating diagram of an embodiment of the process of the invention. The system of FIG. 1 represents different items of equipment which are described successively.

In the remainder of the description, the terms "amplitude" and "acoustic pressure" will be used indifferently.

A "pulse" may be interpreted at the level of the signal as an emission for a certain duration but also as the phenomenon induced locally by this signal. The induced phenomenon corresponds to a local ultrasound thrust resulting from an ultrasound radiation force. This latter thrust is capable of directly exerting a mechanical thrust on the cardiac tissues.

A phased array RES_US makes it possible to generate one or more focussed beams in one or more focussed zones. Each focussed zone is controlled in position, for example, by means of a positioning system SYS_POS dynamically generating a set point to the phased array.

"Focussed beam" designates a set of signals coming from different elements of a phased array of which the frequency and phase characteristics make it possible to generate constructive or coherent interferences in a focussed zone.

The phased array makes it possible, according to the embodiments, to define one or more focussed zones in the heart thanks to a particular configuration of phases of each element of the phased array. The different focussed zones are obtained by making the signals of different elements of the phased array interfere at different points.

The processes of the invention make it possible to carry out measurements of monitoring parameters, such as tissue deformation ACQ_DEF, temperature ACQ_T, electrical activity ACQ_AE or instead the presence of a cardiac contraction ACQ_CONTRACT, during or consequent to the application of the focussed beam. Moreover, the processes of the invention make it possible to measure a representative level of the phenomenon of cavitation ACQ_CAV in or near to the focussed zone as well as a measurement of position or displacement of the targeted zone ACQ_POS.

The terms "tissue deformation" and "tissue displacement" are used indifferently in the description to describe the effect caused by the generation of an ultrasound thrust on the cardiac tissues.

The control of the position(s) of the focussed beam(s) at one or more point(s), called "focussed zone", is carried out by means of a position set point, called "targeted zone".

The mechanism for controlling the focussed beam in a targeted zone is advantageously carried out in synchronisation between the positioning system and the array of beams thanks to the acquisition of the ECG, which constitutes a time reference common to the different items of equipment.

The process of the invention makes it possible to take into account a parameter of displacement of the position set point of the targeted zone $Z_C$ caused by respiratory movements and/or contractions of the heart. A new targeted position is then calculated by means of a computer coupled to the positioning means to adapt the set point to the phased array. According to the process of the invention, the phased array is capable of generating a phase parameter at each signal emitted by an element of the array for deflecting the beam and controlling the focussed point $Z_F$ on the new position of the targeted zone $Z_C$.

Furthermore, apart from respiratory phenomena, contraction movements of the heart subsist, particularly during the QRS complex of the ECG. So as to be able to ignore contraction movements of the heart in the control of the zone focussed on the targeted zone, the focussed beam may:
either be interrupted during the appearance of the QRS complex visible on the ECG;
or be completed by the application of a second deflection correction to compensate for the displacement of the heart during the appearance of the QRS complex.

The invention makes it possible to implement the two solutions during the monitoring process or during the stimulation process.

According to an embodiment, the emitter may comprise a single emitter emitting a signal in the focussed zone.

ECG Acquisition A first step, noted ACQ_ECG, comprises the acquisition of an electrocardiogram, noted ECG, of a patient or an animal from a first electrical system noted SYS_ELEC_1. According to an embodiment, the electrocardiogram makes it possible to acquire the heart beat rhythm, also called the cardiac frequency, which is displayed on a display, noted AFF_1.

According to an embodiment, the acquisition of the ECG is carried out by placing electrodes on the surface of the body of a patient or an animal. This solution makes it possible to measure the electrical activity of a heart in a non-invasive manner. According to an alternative embodiment, the ECG may be acquired using twelve or sixteen derivations according to known modalities of layout and positioning of electrodes.

According to an embodiment, a specific catheter is positioned in a cavity of the heart for the measurement of local electrical activity. In this case, the process of the invention also makes it possible to compare the electrical activities acquired by the electrical catheter and the device making it possible to obtain the ECG. This means is noted SYS_ELEC_2 in FIG. 1.

Synchronisation of Applications

Apart from its display, the ECG is used according to the process of the invention to synchronise different items of equipment together. The synchronisation of the different items of equipment makes it possible to generate synchronised actions in one or more regions of the heart.

The synchronised actions comprise notably:
the ballistic: that is to say the control of the position of the focussed zone $Z_F$ on the position of the targeted zone $Z_C$ or by taking into account for example the frequency of contraction of the heart in the control of the ballistic or the stoppage of the emission of the beams. This synchronisation takes into account movements of the heart as well as, if necessary, the avoidance of the transcostal wall, and/or;
the monitoring: that is to say the measurement of certain monitoring parameters during or consequent to the generation of the beam.

Synchronisation of the Beam

In an embodiment, the generation GEN $F_{US}$ of a beam of focussed ultrasound signals in a targeted zone of the heart and the acquisition of images ACQ IMG are synchronised with the ECG. "Synchronised" from the point of view of the phased array is taken to mean the fact that the generation of the ultrasound beam GEN $F_{US}$ is triggered at a determined time of the ECG. This synchronisation makes it possible to cause a desired physiological effect in a zone of the heart by taking into consideration the state of polarisation of the cardiac tissue. When pulses of ultrasound beams $F_{US}$ are generated periodically, the synchronisation of the pulses with the ECG makes it possible to cause stimulation in a same state of polarisation of the cardiac tissues at each emission.

The synchronisation of the ECG and the phased array is thus configured to obtain a desired effect of the beam on a zone of the heart according to the envisaged application. That is to say that the generation of the focussed beam is generated in a time window corresponding to a depolarisation or a repolarisation of a ventricle or an auricle according to the specific case.

Synchronisation of Imaging

As regards the acquisition of at least one image ACQ IM, it is also to preferentially synchronised with the ECG. That is to say that the image is acquired at given times of the ECG. The times of acquisition of an image with regard to the ECG may be configured by an operator or may be deduced automatically as a function of a synchronisation set point.

Acquisition of Images

A second step, noted ACQ IMG, comprises the acquisition of at least one image of a region of the heart, by an imaging system noted IMG, in which a targeted zone $Z_C$ is located, noted ACQ_$Z_C$.

According to an embodiment, the acquisition of the image is carried out by means of an MRI imaging system. Based on the magnetic properties of atoms, MRI imaging system consists in applying a magnetic field to the atomic nuclei then stimulating said atomic nuclei by radiofrequencies. The reconstitution of an image is then possible from the signal emitted during the relaxation phase and collected by electromagnetic sensors.

Advantageously, the MRI imaging system, coupled with a computer K1, makes it possible to:
define a position of a targeted zone $Z_C$ as a set point for controlling the phased array of focussed signals; the position of the targeted zone $Z_C$ may also be defined by another positioning equipment or be transmitted to such an equipment;
deduce tissue deformation and/or a variation in tissue deformation near to or in the focussed zone, the MRI in this mode is more commonly known as MRI-ARFI; MRI-ARFI makes it possible to measure the hardness or the elasticity of the tissues following a rise in temperature in an identified zone,
deduce a temperature and/or a variation in temperatures near to or in the focussed zone, MRI in this embodiment is more commonly known as MRI-T,
determine the projection of the transcostal wall of a patient in the image plane of the phased array to activate or deactivate the elements of the phased array capable of causing damage to the bone wall by taking into consideration a parameter of deflection of the beam.

According to another embodiment, the invention comprises an acquisition of an image by means of an ultrasound imaging system. This system may be used in addition to an MRI imaging system or as a substitute thereof for tissue displacements measurements. An ultrasound imaging system, called echocardiography, is based on the emission of acoustic waves in the body. Said waves are reflected differently according to the type of anatomic structures encountered. The signal collected, corresponding to the echoes of the waves emitted, makes it possible to reconstitute an image of a part of the anatomy of a patient or an animal.

According to another embodiment, the acquisition of an image is carried out by means of an X-ray imaging system. This imaging system is based on the emission of X-rays on the tissues. The measurement of the attenuation of the X-rays by the tissues makes it possible to reconstitute images in 2D or 3D of anatomical structures such as for example the heart. This system may be used in addition to an MRI imaging system or as a substitute thereof for ballistic measurements, that is to say the position of the focussed zone. The targeted zone $Z_C$ may be potentially defined from the imaging system.

According to another embodiment, the acquisition of an image is carried out by means of a positron emission imaging system (TEP), called tomoscintigraphy. This imaging system is based on the detection of gamma radiation emitted by a radioactive substance injected in small amounts into the body, which makes it possible to acquire images in section of certain organs such as for example the heart. This system may be used in addition to an MRI imaging system or as a substitute thereof for ballistic measurements, that is to say the position of the focussed zone and/or the targeted zone. The targeted zone $Z_C$ may be potentially defined from the imaging system.

The imaging systems may be, if need be, coupled with injected or ingested contrast agents, so as to improve the visualisation of the organs explored.

Positioning System

A positioning system is used during the execution of the processes of the invention to fulfil different functions:
- a first function is to define the position of a targeted zone $Z_C$ that it is wished to reach. For this purpose, according to an example, the positioning system may be coupled to an imaging system to recover, on the acquired image ACQ_IMG, the position of an identified targeted zone $Z_C$,
- a second function is to calibrate the ballistic of each device or system realising a function of the processes of the invention. Thus, the imaging systems and the phased array may be calibrated in position with a positioning system.
- a third function is control of the position of the focussed zone $Z_F$ on the position of the targeted zone $Z_C$. To do so, a set point is generated to the phased array so that the beam is correctly deflected.
- a fourth function is to generate a set point of activation or deactivation of the elements of the phased array in accordance with the projected position of the transcostal wall in the plane of the phased array. This function may be assured directly by the imaging system to the phased array. The use of the positioning system may make it possible to improve the speed of control without having to be limited by the acquisition time of the image. In the latter case, the calculations of the positions of the projected image of the transcostal wall may be memorised in the positioning system and changes in the positions of the patient may be calculated from a reference position.

According to an embodiment, the positioning system comprises extracorporeal ultrasound sensors and an extracorporeal emitter of which the emissions of ultrasound signals are reflected and detected by the sensors. A given position ACQ_POS of the heart may be obtained by triangulation. Four sensors of signals make it possible to obtain good precision of the positions of zones in the heart. An advantage of this solution is that the control of a position in space may be quicker than by the use of an imaging system. Indeed, this solution requires less data to acquire and to process. The receptors acquire the variations on a line of the 3D space.

According to an alternative embodiment, the emitter is an emitter dedicated to the positioning system. According to another alternative embodiment, the emitter may be for example an element of the phased array notably to establish the calibration of the start position.

The receptors of the phased array may be used. To improve the precision of the measurements, ultrasound wave sensors dedicated to the positioning system are preferred.

In another embodiment, the positioning system is realised by means of sensors positioned on the skin. When the position of the focussed zone $Z_F$ or the targeted zone $Z_C$ is determined from an imaging system IMG, according to an exemplary embodiment, it may be recognised automatically from image processing. To this end, an indicator based on variations in parameters relative to the pixels of the image may be generated to recognise automatically a specific zone of the heart. According to another exemplary embodiment, the targeted zone $Z_C$ may be identified by means of an image processing tool with usage of a mouse or a graphic pointer. The targeted zone $Z_C$ may also be designated by the definition of space coordinates of a two-dimensional or three-dimensional image, for example from software configured to guide the phased array.

According to an embodiment, the position of the targeted zone $Z_C$ may be determined using an intracardiac catheter including an ultrasound or electromagnetic probe introduced into a ventricle or an auricle of the heart and coupled respectively with one or more ultrasound position sensors or with one or more electromagnetic position sensors. Said positioning system may thus be associated with an MRI imaging system or at least one ultrasound probe or instead at least one intracardiac sensor. An ultrasound probe makes it possible, according to an embodiment, to define the targeted zone $Z_C$ to control the position of the focussed beam and thus the focussed zone $Z_F$. This system may be used in addition to an MRI imaging system or as a substitute thereof for tissue displacement measurements.

The positioning system makes it possible to define a position of the targeted zone $Z_C$ which is transmitted to the phased array RES_US or to the generator of ultrasound signals for the control in position. Secondly and potentially, the positioning system is capable of recovering the position of the focussed zone $Z_F$ to deduce therefrom a difference with the position set point of the targeted zone. The positioning system may thus be integrated in an imaging system by a function implemented in a computer or be external to the imaging system and be associated therewith to extract data from the acquired image.

According to an embodiment, the process of the invention makes it possible to identify one or more targeted zones $Z_C$. This step makes it possible to fulfil different functions of which the control of the focussed zone $Z_F$, as described previously.

A possible function of the process of the invention comprises a comparison of the imaging data of the targeted zone $Z_C$ or of a zone near to it before and after the cardiac stimulation to determine a parameter of tissue deformation and/or a parameter of variation in temperature. Indeed, when a comparison of images is carried out, the process of the invention makes it possible to identify a gradient of values in the image, that is to say a variation translating for example a displacement of cardiac tissue and/or a variation in temperature. This is notably the case when the imaging system is an MRI imaging system and when it is coupled to a computer K1. After the application of a magnetic field, the latter makes it possible to deduce a dephasing parameter comprising a value relative to the displacement of the tissues and a value relative to the variation in temperature. The computer K1 makes it possible notably to conduct image processing operations to monitoring parameters.

Phased Array, Generator of Signals

A third step, noted GEN $F_{US}$, comprises the generation of one or a plurality of beam(s) of focussed ultrasound signals $F_{US}$ focussed in the targeted zone(s) $Z_C$.

The therapeutic ultrasound probe is mounted on a 3D mechanical positioning system making it possible to locate the probe directly in line with the targeted cardiac region. Thanks to phased array technology, the ultrasound beam may be deflected electronically around the natural position of the focal point for a fine adjustment of the shot zone. This makes it possible to target easily different regions of the heart to stimulate several distinct zones with a managed time delay between each shot.

According to an exemplary embodiment, a phased array with 256 elements may be used with a central frequency at 1 MHz. The geometric focus may be configured at 13 cm.

In one embodiment, the phased array RES_US of focussed ultrasound signals $F_{US}$ comprises a set of elements, such as elementary transducers. The configuration of the phased array RES_US enables the activation or the deactivation of the elements, and the parameterisation of the phases of each signal which makes it possible to guide the deflection of the generated beam. The position of the focal point of the beam is thus determined by the parameterisation of the phases of each signal defining a given deflection.

The configuration of the phased array makes it possible to take into account obstacles between the elements of the phased array RES_US and the heart, such as the ribs or other organs. Thus, it is possible to configure the generation of one or more beam(s) while avoiding the obstacles. This makes it possible, for example, not to damage the ribs of a patient. The stimulation method of the invention is particularly efficient when the array RES_US is positioned facing the thoracic cage, the closest to the heart. In this configuration, the process of the invention makes it possible to establish a configuration of the phased array RES_US in order to avoid insonifying the ribs, since burns can be induced by absorption of emitted ultrasound waves in a bone wall.

This configuration may be realised during the calibration of a focussed beam or during the operation of stimulation of at least one zone of the heart. The deflection of the beam may be controlled to compensate for respiratory movements or contractions of the heart inducing a displacement of the targeted zone. A new position of a targeted zone may be determined by an estimation of the displacement of this zone thanks to a positioning system, as detailed previously.

The targeted zones $Z_C$ define a region in the reference frame of the heart and are thus capable of moving in a terrestrial reference frame. The phased array thus has to compensate for movements of the heart induced by respiratory movements or contractions of the heart. This is achieved thanks to the control of the focussed position $Z_F$ on the targeted position $Z_C$.

In particular, according to an embodiment, the deflection of the beam is controlled on a parameter of compensation of respiratory movements of the heart. Indeed, the respiratory movements generate displacements of the targeted zone $Z_C$ throughout the cardiac cycle and are preferentially compensated during the execution of the processes of the invention.

Optionally, according to an improved embodiment, the deflection of the beam may be controlled on a parameter of compensation of contraction movements of the heart occurring during the QRS complex. An alternative is to automatically switch off the beam during the appearance of the QRS complex to avoid burning, for example, during the stimulation method or to stimulate a zone related to the targeted zone $Z_C$. In this case, the extinction of the beam is controlled on the rhythm of the ECG so that the moments of appearance of contraction and extinction of the beam are synchronised.

In an embodiment, the beam of focussed ultrasound signals $F_{US}$ is configured to generate a pulse on a targeted zone $Z_C$ so as to stimulate the cardiac tissues in this zone. The process of the invention makes it possible to observe the electrical response and/or the tissue deformation and/or the temperature and/or a level of cavitation in or near to said zone. When the stimulation is carried out on a single targeted zone $Z_C$, it makes it possible, for example, to test the electrical activity of said zone.

The phased array RES_US may also be used as ultrasound positioning device for calibrating the position of a focussed zone $Z_F$ with an imaging system IMG. Other applications are possible and are described hereafter.

Multi-Beam(s)

In an embodiment, the phased array RES_US is configured in phase to generate a plurality of focussed beams and thus generate a plurality of pulses in several targeted zones $Z_C$. It is then possible to stimulate said zones and observe the electrical responses and/or deformations and/or temperatures and/or levels of cavitation of said zones and thus potentially carry out a comparison of the responses. When the stimulation is carried out on a plurality of targeted zones $Z_C$, it makes it possible, for example, to calibrate the levels of the signals in different zones to schedule stimulation operations. According to another example, the multipoint stimulation engaged simultaneously makes it possible to carry out an operation of resynchronisation of the ventricles or the auricles or instead to modify the heart beat frequency. Other applications are possible.

Definition of Signals

In all the embodiments, the beam of focussed ultrasound signals $F_{US}$ is generated at a configured amplitude and for a configured duration so as to monitor the levels of mechanical and/or thermal damage to cardiac tissue.

Within the scope of a cardiac stimulation application, a configuration is sought enabling the best stimulation and the least damage to tissues. A calibration of the signals according to the monitoring process of the invention may be carried out to prepare a stimulation phase in which the signals define one or more optimised beams. The optimisation is carried out by calibrating the amplitude, the duration and the repetition of the pulses of the focussed beam. The calibration depends on different criteria: age, corpulence of the patient, size of the heart, thickness of the cardiac tissues, myocardium, stimulated zones, etc. The calibration of the signals thus makes it possible to adapt a beam to define an efficient stimulation.

In an embodiment, the phased array of ultrasound signals comprises a set of elements, such as elementary transducers. The configuration of the phased array enables the activation or the deactivation of the elements, and the parameterisation of the phases of each signal makes it possible to guide the deflection of the beam. The position of the focal point of the beam is thus determined by the parameterisation of the phases of each signal defining a given deflection.

The configuration of the phased array makes it possible to take into account obstacles between the elements of the array and the heart, such as ribs or other organs. Thus, it is possible to configure the generation of one or more beam(s) while avoiding the obstacles. This makes it possible, for example, not to damage the ribs of a patient. The stimulation method of the invention is particularly efficient when the array is positioned facing the thoracic cage, the closest to the heart. In this configuration, the process of the invention makes it possible to establish a configuration of the phased array in order to avoid insonifying the ribs to avoid any burning induced by the absorption of the emitted ultrasound wave in a bone wall.

This configuration may be realised during the calibration of the focussed beam or during the operation of stimulation of at least one zone of the heart.

The process of the invention makes it possible to configure two modes of cardiac stimulation that may be used:
  either to calibrate the signals with a view to a specific application, notably by generating a pulse and by analysing the associated response,
  or to stimulate directly a targeted zone to obtain a physiological effect by generation of a pulse train.

In a first embodiment, the amplitude of one or more pulses is less than a first given amplitude threshold and the duration of the pulse or said pulses is greater than a given duration threshold.

This first embodiment is particularly advantageous for stimulating a zone or zones of the heart while monitoring to ensure that mechanical damage does not arise in the tissues. This embodiment enables controlled heating of the targeted zone $Z_C$ without nevertheless causing thermal damage. Thermal damage is limited by monitoring the duration of application of the beam. This first embodiment concerns more particularly the pulses represented in FIG. 6A.

In a second embodiment, the amplitude of one or more pulses is above a second given amplitude threshold and the duration of the pulse(s) is less than a given second duration threshold.

This second embodiment is particularly advantageous for stimulating a zone or several zones of the heart while monitoring to ensure that thermal damage does not arise in the tissues. Thermal damage does not arise due to the fact that the pulse, if it is sufficiently short, does not cause heating of the zone. The stress is relaxed on mechanical damage that can occur with pulses of greater amplitudes than in the first embodiment, that is to say of which the intensity of the radiation force generated by the ultrasound beam is greater than that of the first embodiment. In this case, the monitoring process of the invention makes it possible to determine an amplitude threshold for which the pulse does not generate mechanical damage of the tissues of the focussed zone or of a neighbouring zone.

This first embodiment concerns more particularly the pulses represented in FIG. 6B.

Figure 4:
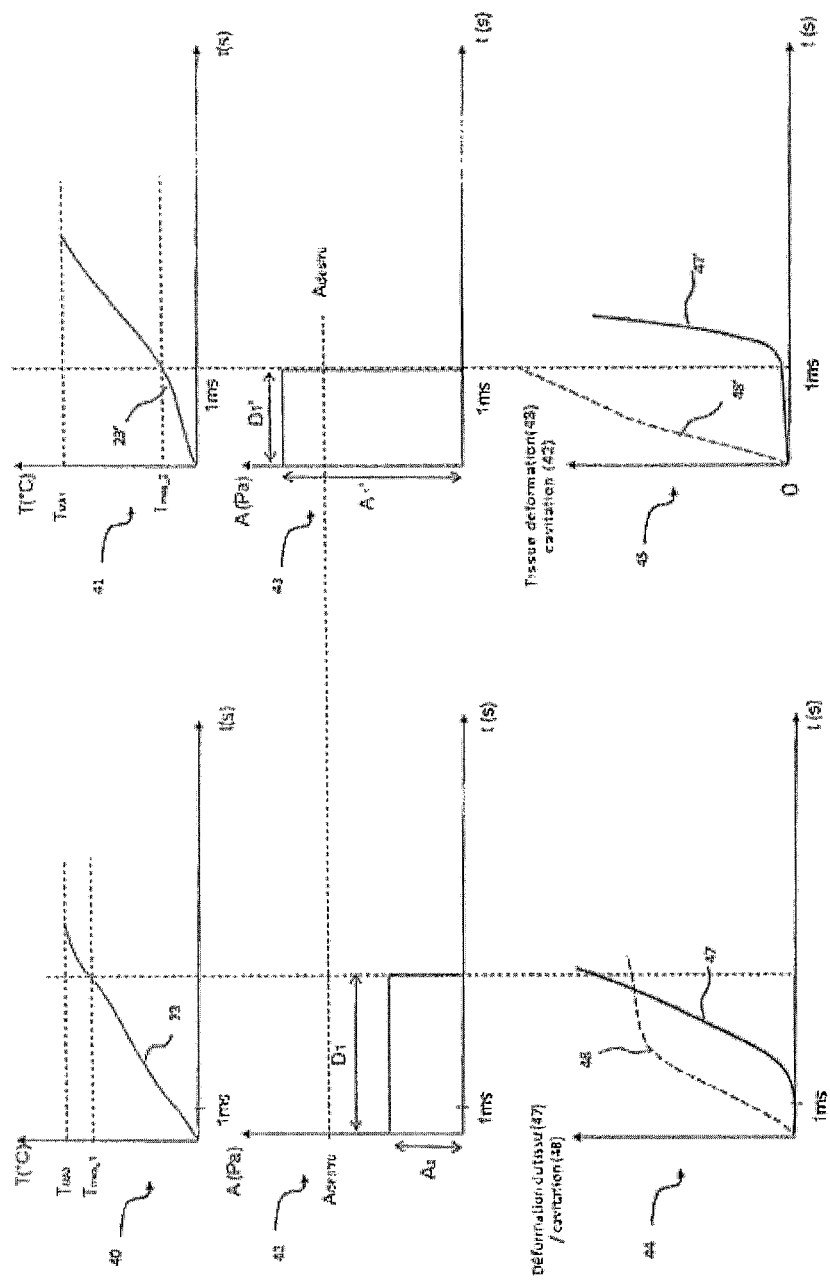
FIG. 4: diagrams representing the evolution of the temperature, the deformation of the tissue at the level of the targeted zone of the heart according to the amplitude and the duration of the pulses of a beam of ultrasound signals in said zone.
Figure 5B:
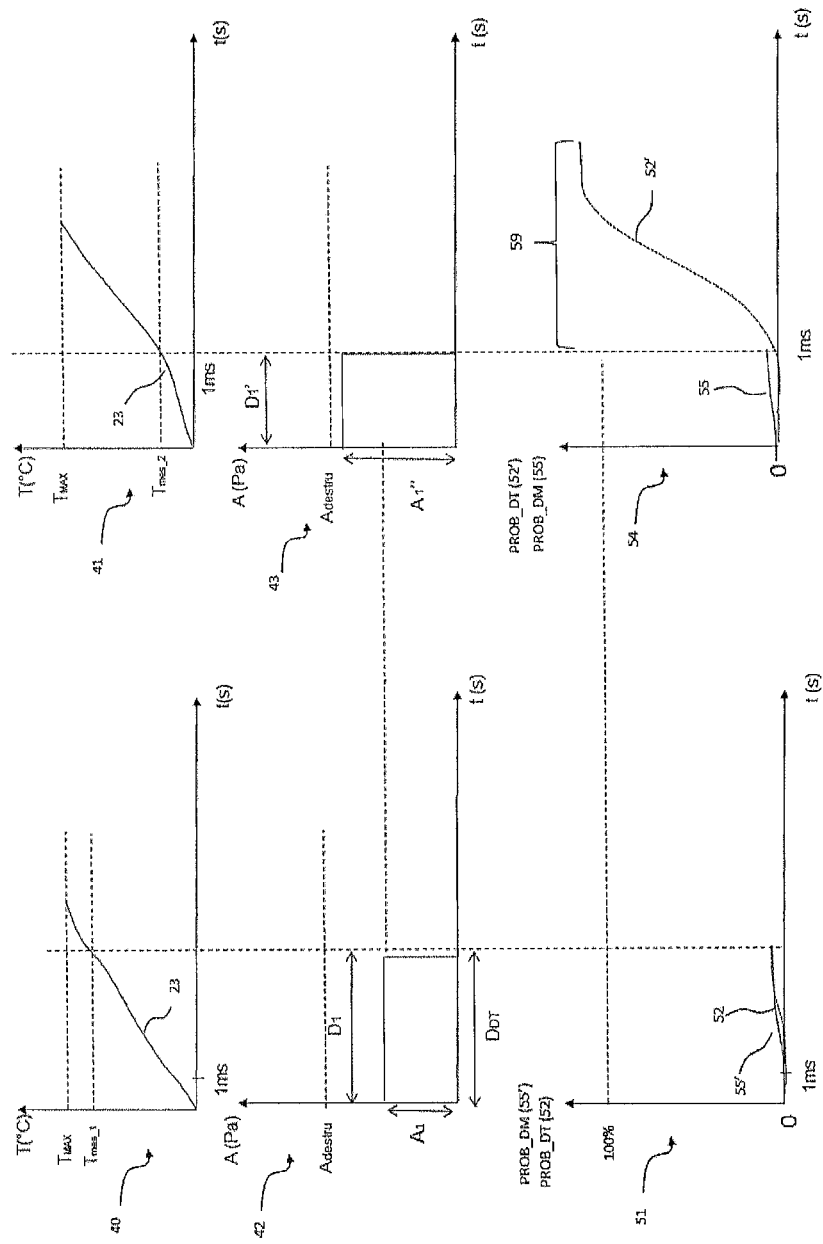

According to an exemplary embodiment, the first amplitude threshold is identical to the second amplitude threshold: $A_{destru}$ and the first duration threshold is identical to the second duration threshold: $T_{destru}$. The thresholds are represented in FIGS. 4 and 5A, 5B in which single thresholds respectively in temperature $T_{destru}$ and in amplitude $A_{destru}$ are represented.

According to an embodiment, the process of the invention comprises a step of injection of an ultrasound contrast agent into the organ, that is to say the heart.

According to a first embodiment, the ultrasound contrast agent makes it possible to visualise the ultrasound beams and to follow the treatment using an ultrasound imaging system. According to this embodiment, the ultrasound contrast agent may be used in combination with an ultrasound imaging device in the same way as a contrast agent is used to improve the visualisation of MRI images. This usage makes it possible for example to detect healthy zones and pathological zones.

According to a second embodiment, the ultrasound contrast agent may be used to favour the action of the focussed ultrasound beam. The presence of the contrast agent makes it possible to improve the appearance of a phenomenon of cavitation when a signal is focussed by the generation of microbubbles. The appearance of this phenomenon being favoured, a consequence is to reduce the threshold of the maximums of amplitude of the acoustic signals favouring the stimulation of tissue in a focussed zone. In this context, the contrast agent makes it possible to reduce the minimum thresholds of the levels of ultrasound signals used to stimulate a zone of the heart. The ultrasound contrast agent thus makes it possible to reduce the power levels emitted by the beam generator while obtaining a result equivalent to that with a higher power without ultrasound contrast agent.

An interest of this solution is to reduce the emitted power levels and thus to reduce the risks of damage to tissues stressed by the ultrasound pulses. Another interest is to reduce damage caused to other organs or to bones by emissions of the beam.

A device that could be used may be for example that designated "SonoVue" from Bracco.

The administration of the ultrasound contrast agent may be injected over a wide range of values. Tests carried out on pig hearts have made it possible to validate the improvement of the generation of a stimulation with acoustic pressure power levels lower than when an ultrasound contrast agent was used. These data are of a same order of magnitude as those that can be obtained in humans. As an example, an injection ranging from 0.03 or 0.20 ml/kg of SonoVue may be used to obtain an effect of improvement of the effect of stimulation of the tissues by application of a focussed beam. A value of 0.1 ml/kg leads to a conclusive result according to tests conducted with focussed acoustic signals producing an amplitude of 2 to 15 MPa over pulse periods shorter than 80 ms.

In this test, the half-life of terminal elimination was 12 minutes (ranging from 2 to 33 minutes).

The use of an ultrasound contrast agent makes it possible to obtain reductions in the power levels required to generate a stimulation in the focussed zone ranging from several hundredths of MPa to several MPa. The gains obtained depend on the quantity of ultrasound contrast agent administered, the period at which the beam is emitted after the administration of the contrast agent and physiological data of the organ specific to the patient or the animal.

Another advantage is that the effect of the ultrasound contrast agent is independent of the duration of the pulse of the beam, which guarantees a common operating procedure, that is to say with the same power levels, for different pulses generated throughout the period during which the contrast agent produces an effect.

Monitoring of Temperature

The process of the invention makes it possible to monitor certain parameters such as temperature ACQ_T in one or more zones of the heart for monitoring said zones during calibration or stimulation operations. A display AFF_2 makes it possible in an embodiment to visualise, in section, in slice or 3D zone, the temperatures of the heart or at least one particular region thereof.

FIG. 1 represents a single display AFF_2 pooling the displays of different items of equipment of which the display of the images acquired. According to another embodiment, different displays may be used and dedicated to each item of equipment in the processes of the invention.

A computer, noted K1, makes it possible to extract the data acquired by imaging IMG, such as an MRI, to deduce the temperatures in certain zones of the heart. An extraction of the position of the targeted zone or the focussed zone may be carried out to identify the temperature in this zone or near to it. For example, the computer K1 is capable of calculating variations in temperatures by an analysis of the data of the image acquired and to identify automatically the zones for which the variations exceed a temperature threshold. The positions of the focussed zones may thus be deduced automatically by processing of the data of the image acquired in MRI.

When the temperature variations are visible on the screen, a colour code may help an operator to avert significant temperature rises.

According to a first embodiment, the monitoring of the temperature may be carried out during the execution of the monitoring process of the invention for calibrating the focussed beam used during the stimulation operation.

According to a second embodiment, the monitoring of the temperature may be carried out during the execution of the stimulation method for therapeutic application. In this case, the term "active monitoring" is used. This active monitoring notably makes it possible to track the heating of the targeted zone as well as zones adjacent to the targeted zone.

Monitoring of Electrical Activity

In an embodiment, a measurement of electrical activity, noted ACQ_AE, may be carried out during and/or after the generation of the beam of focussed ultrasound signals GEN $F_{US}$ in addition to the measurement of tissue deformation and/or temperature and/or level of cavitation so as to verify the efficiency of the ultrasound stimulation in or near to the focussed zone. The electrical activity ACQ_AE may be measured locally from a catheter or from the electrical system making it possible to obtain the ECG.

The electrical response times and/or the level of electrical activity in or near to the focussed zone may be measured from a dedicated electrical equipment noted SYS_ELEC_2 and represented in FIG. 1. It makes it possible to acquire the signal ACQ_AE translating a level of local electrical activity. A computer K2 may be added to the system. It enables the implementation of an embodiment of the invention, by comparing a level of electrical activity with a reference level or instead to reconcile the values of level of electrical activity with the measurement of tissue deformation ACQ_DEF. These correlations/comparisons of values are represented by the function COMP in FIG. 1. A message of state VERIF_2 makes it possible to end up with the result of the comparison. According to another embodiment, the functions realised by the computer K2 may be assured by the computer K1.

According to an embodiment, the level of electrical activity may be measured from an electrical catheter introduced into a region of the heart: ventricle or auricle.

According to other embodiments, other items of equipment may be used making it possible to measure electrical activity locally in or near to the focussed zone.

It should be noted that local electrical activity ACQ_AE in the targeted zone may be monitored and deduced from the ECG obtained for example using electrodes. In this latter specific case, the electrical systems SYS_ELEC_1 and SYS_ ELEC_2 of FIG. 1 may only form a single item of equipment. Notably, when a stimulation is generated by the stimulation process of the invention and when a global depolarisation of a ventricle or an auricle takes place, then the electrical activity induced by the stimulation method is visible on an ECG by the presence of a peak. In this case, an electrical catheter may potentially be used to correlate the measurements of electrical activities deduced from the ECG or to obtain more precise measurements.

In an embodiment, a pulse is applied in a targeted zone $Z_C$ of the heart during the repolarisation of cardiac tissue. A measurement of the electrical activity of the heart and/or tissue deformation and/or level of cavitation and/or temperature induced by the pulse in the targeted zone $Z_C$ of the heart is or are carried out. Depending on the electrical response, the measured deformation and/or temperature and/or level of cavitation, a calibration of the beam of ultrasound signals $F_{US}$ is carried out. Different values of amplitudes and durations of the pulse may be configured while monitoring that the temperature does not exceed locally a threshold, beyond which damage to tissues may occur.

In an application for cardiac resynchronisation, this monitoring makes it possible to determine the positions of placement of probes having good electrical response properties. The probes are intended to be fixed onto the wall of the myocardium and to generate cardiac pulses at a plurality of points of the heart of a patient. The pulses thereby generated ensure the synchronisation of the ventricles or the auricles of the heart.

When the deformation of the cardiac tissue or the electrical activity of the focussed zone is less than a predetermined threshold for a given amplitude and duration of at least one pulse of the focussed beam $F_{US}$, the focussed zone is then considered as "non-responding".

According to a first monitoring, when the focussed zone is considered as non-responding, the monitoring process of the invention makes it possible for example to adjust in duration and in amplitude a new focussed beam to carry out a second calibration measurement.

In this case, the process for calibrating a focussed beam makes it possible to define a new focussed beam notably taking into account variations in temperatures in order to avoid damaging tissues with the new beam applied in the focussed zone.

According to a second monitoring consecutive to an ablation operation, when the focussed zone is considered as non-responding, the monitoring process makes it possible, for example, to verify that an ablation of a zone generating an arrhythmia has gone well.

It is possible to deduce a theoretical level of electrical activity generated as a function of the measured level of tissue deformation. Thus, according to an embodiment of the invention, the monitoring and stimulation process do not require a measurement of the electrical activity, since it may be deduced from a tissue deformation measurement. The processes of the invention may thus advantageously be non-invasive.

The calibration process may comprise a step of calibration making it possible to establish a correspondence rule between the levels of electrical activities and the levels of tissue displacements measured during the application of a focussed beam in a given focussed zone. This calibration may also take into account the responses to temperatures in this zone.

During the stimulation method, this calibration makes it possible to measure uniquely the levels of deformation of tissues and to deduce the electrical activity induced.

When the measurement of the deformation of tissues, or a characteristic specific to their elasticity, is small, or even zero, then it is possible to deduce that no electrical activity is generated.

Monitoring Cardiac Contraction

Finally, the stimulation method of the invention may comprise a step of verification of the presence of a cardiac contraction. The verification of a mechanical contraction may be carried out by means of a blood pressure probe, for example by a measurement of the heart pulse, or by an intra-aortic probe to measure the contraction of the heart. This equipment for measuring mechanical contraction is noted CAP_CONTRACT in FIG. 1 and the measurement is noted ACQ_CONTRACT.

The monitoring of cardiac contraction is particularly interesting for an application of the process of the invention with a mobile or portable device, for example integrated in an emergency services vehicle. The portable device of the invention in this embodiment does not comprise an imaging system. Conversely, the mobile device makes it possible to measure the presence of a contraction of the heart to verify that one or more stimulations applied to a patient have indeed generated a physiological effect.

Figure 2:
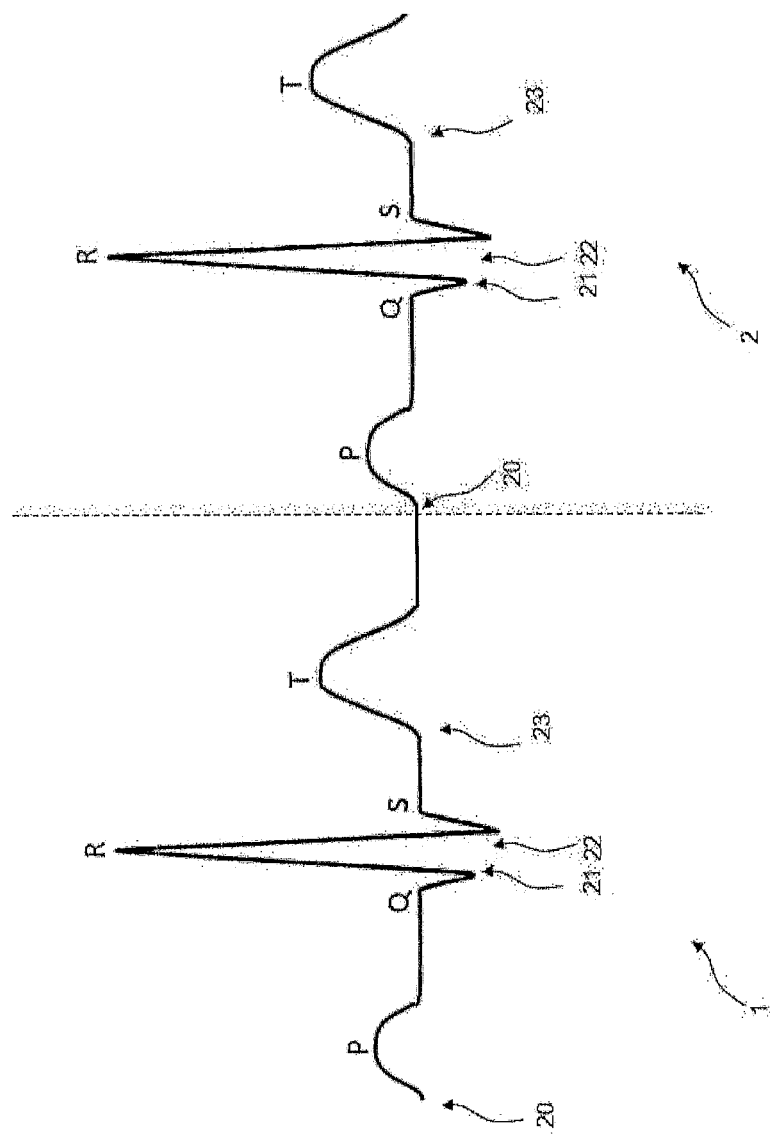
FIG. 2: an example of a sequence of an electrocardiogram of the heart.

FIG. 2 illustrates an example of a sequence of an ECG of the heart. The sequence of the electrocardiogram represented comprises two contractions 1 and 2 of the myocardium.

The wave P which begins at the time 20 corresponds to the depolarisation of the auricles, followed by the QRS complex which comprises the depolarisation of the ventricles, which begins at the time 21, and the repolarisation of the auricles, which is merged with the QRS complex and finally the T-wave corresponding to the repolarisation of the ventricles at the time 13.

Monitoring of Cavitation

According to an embodiment, the monitoring process as well as the stimulation process of the invention comprise a step of calculating a level of cavitation in the focussed zone. The phenomenon of cavitation is based on the phenomenon of creation of bubbles in the focussed region generated by the vibration of the ultrasound waves emitted.

Two cavitations that may occur may be distinguished:
a stable cavitation, which corresponds to a phenomenon of creation of bubbles in the focussed zone or near to it. The bubbles potentially favour the displacement of tissues;
an inertial cavitation, which is in the continuity of stable cavitation, in which the bubbles vaporise or burst, which can create damage to tissues but which can also stimulate the zone. The phenomenon of inertial cavitation is created by generation of a negative pressure locally beyond a certain threshold.

The phenomenon of cavitation may be determined by a device for measuring a level of cavitation. According to an exemplary embodiment, it may be an ultrasound device for the detection of a level of cavitation ACQ_CAV in or near to the focussed zone, noted SYS_CAV in FIG. 1. This device comprises a sensor or several sensors of ultrasound waves and a computer carrying out a spectral analysis ACQ_US of the ultrasound waves reflected in or near to the focussed zone.

According to an embodiment, a computer K1 makes it possible to centralise the different measurements carried out by different items of equipment, of which the measurements of the level of cavitation ACQ_CAV, tissue deformation ACQ_DEF, temperature ACQ_T. The measurements are potentially compared to thresholds. Alarms may be generated according to predefined thresholds of these measurements being exceeded in real time. A display AFF_2 potentially makes it possible to display these values and the images acquired by the different items of equipment.

According to another embodiment, each item of equipment may be coupled to a dedicated computer and a dedicated display.

The more the spectrum is spread out, that is to say the higher the noise in or near to the focussed zone, the more the phenomenon of cavitation is determined as important. Thresholds may be defined and determined from the monitoring process of the invention for calibrating the values of amplitudes and durations of the signals used notably for the stimulation for different cardiac applications.

According to an embodiment, the monitoring carried out during the execution of a stimulation method detects in real time a level representing the importance of the phenomenon of cavitation. The stimulation method may dynamically take into account the measured levels:
either to stop the beam or the beams, if the high level is too high;
or to configure automatically the level of pressure generated at the focal point by a pulse duration amplitude set point.

The phenomenon of cavitation in the targeted zone may also be measured by the processes of the invention:
either by extrapolation of tissue deformation essentially generated by this phenomenon;
or by extracorporeal ultrasound sensors, as specified previously, by spectral analysis of the reflected signals;
or by an intracardiac ultrasound sensor positioned near to the targeted zone.

According to another embodiment, which can be combined with the preceding embodiments, a measurement of a level of cavitation is compared to a first threshold and a measurement of a tissue deformation is compared to a second threshold.

When the level of cavitation exceeds the first threshold, a first risk of damage is identified. When the measurement of tissue deformation exceeds the second threshold, a second risk of damage is identified. An algorithm making it possible to take into account the two risks may make it possible to generate a set point for stopping the calibration or stimulation procedure, for example by automatically cutting the ultrasound signal emitted. An interest is to reinforce the safety procedure governing an intervention aiming to stimulate a zone of the heart or to improve the detection of a risk.

Finally, another interest resides in the possibility of obtaining a double indicator over time based on a double risk assessment by two different means. Indeed, an ultrasound sensor measuring the level of cavitation may acquire between 10 and 5000 signals per second, whereas a tissue deformation sensor, using for example MRI, will require an acquisition refresh rate of 0.5 to 10 signals per second. It is thus possible to have available a system comprising calculation means making it possible to carry out a first measurement of the level of cavitation and when a first risk is identified, then a detection of the evolution of the level of deformation may be analysed in the time span succeeding the detection of the first risk identified. Hence, it is possible to generate a cut off of the focussed signal as quickly as possible.

Furthermore, the first exceeding of the level of cavitation may lead to analysing the evolution of tissue deformation without all the same the second threshold being exceeded. The analysis then concerns the tendency of the tissues to deform and not the exceeding of a second given threshold. Thus, it is possible, thanks to the process of the invention, to cut off the generation of the signal as quickly as possible.

According to an alternative, the measurement of the level of cavitation is no longer correlated with the measurement of tissue deformation but with electrical activity in or near to the focussed zone. In the latter case, the same processing may be applied to these two measurements, notably as regards the analysis of the signals by the different items of equipment over time.

The algorithm may also enable the generation of a cut off of the ultrasound signals uniquely when two thresholds are exceeded, a first threshold concerning the level of cavitation and a second threshold concerning, for example, the deformation of tissues. This other option makes it possible to consider measurements errors of measurement apparatuses, such as MRI or an ultrasound device for example.

The process of the invention thus makes it possible to define different strategies for monitoring the stimulation of a zone to avoid causing damage during such an operation. A first strategy may correspond to ensuring a maximum degree of safety. In this case, a single exceeding of a threshold makes it possible to generate a cut off of the beam of signals. A second strategy corresponds to ensuring the elimination of measurement errors. In this case, the process makes it possible to confirm that damage occurs if two thresholds of measurements of different items of equipment are exceeded.

It may be noted that the process applies with a plurality of measurements corresponding to quantities measured with different items of equipment.

Thus, a correlation of three types of signals may be carried out by making comparisons with regard to three thresholds. For example, the level of cavitation is compared to a first threshold, tissue deformation is compared to a second threshold and electrical activity is compared to a third threshold. A monitoring strategy may be that exceeding two thresholds out of three suffices to generate a cut off of the ultrasound signals. This solution enables a compromise between a gain in safety (2 apparatuses out of 3 have detected a risk) and taking into account measurement errors (1 apparatus out of 3 has detected nothing). Other possibilities may be decided depending on whether a configuration favouring maximum safety is desired: at least one threshold being exceeded leads to the cut off of the beam or depending on whether a configuration in which measurements errors are taken into account is desired: the three thresholds have to be exceeded to bring about a cut off of the beam.

Monitoring of Tissue Displacements

The generation of the beam(s) of ultrasound signals GEN $F_{US}$ makes it possible to generate a localised ultrasound thrust in a focussed zone $Z_F$ and possibly substantially near to this zone by displacement of tissues.

The ultrasound thrust may be accompanied by secondary phenomena which are linked, or not, to the generation of this thrust. A first phenomenon is linked to the molecular agitation induced by the beam at the focussed point. A second phenomenon is linked to the cavitation induced by the focussed beam.

The phenomenon of cavitation is behind the creation of microbubbles in or near to the focussed zone, which can:
  either improve the effect of displacement of tissues or the propagation of electrical activity induced by the contraction of the tissue, the term stable cavitation is used,
  or destroy the tissues by generation of a negative pressure locally beyond a certain threshold. Beyond a negative pressure threshold, the destruction of bubbles or their vaporisation thus creates lesions in the tissues, in this case the term inertial cavitation is used.

The process of the invention, according to the configuration of the ultrasound signals, is capable of generating a displacement of tissues by favourably controlling the effects of cavitation in order to avoid the destruction of tissues.

One interest is that the phenomenon of cavitation may induce mechanical stress applied to the tissue in addition to the ultrasound radiation force being able to induce electrical activity.

When the pulses are generated for a duration less than a given threshold, corresponding to pulses of short duration, then it is possible to induce electrical activity while minimising heating of the focussed zone.

The displacements of the tissues may be obtained thanks to an imaging system such as an MRI imaging system. In this case, an advantage is that a single item of equipment makes it possible to obtain the positions of the targeted zone and the focussed zone, and a quantification of the variations in temperatures and displacements of the tissues.

When the measurements of temperatures and deformations of tissues are carried out by a single MRI imaging equipment, which is possible thanks to the intrinsic difference between dephasing due to a change in temperature and that due to a local displacement, these two effects may be discriminated and measured simultaneously. This solution is thus advantageous from the point of view of the number of items of equipment used and the simplification of the calculations to implement to deduce tissue deformation data and temperature data from the same acquisition.

The coupling of these two items of equipment thus makes it possible to follow simultaneously the temperature and the displacement of cardiac tissue by a single acquisition method.

Finally, the measurement of tissue deformation makes it possible to calibrate the levels of elasticity of the tissue in a targeted zone during the monitoring process, for example to record that a coagulative necrosis has finished. Moreover, when the monitoring process makes it possible to verify that an ablation has gone well, a comparison of the levels of elasticity during the ablation with a measurement carried out beforehand makes it possible to quantify the proportion of zone ablated as a function of a level to reach.

Tissue deformations may be measured from an MRI imaging system as specified previously. Other imaging systems may be used when the latter make it possible to monitor deformation or elasticity of the tissue. According to another embodiment, tissue deformations may be measured by a catheter comprising an ultrasound probe introduced near to the focussed zone ($Z_F$) measuring tissue deformation. Optionally, a catheter comprising a pressure probe may be used near to the focussed zone to deduce tissue deformations.

According to an embodiment, as for the measurement of temperature variations, the computer K1 makes it possible to recover the position of the targeted zone by recovering the position set point or the position of the focussed zone $Z_F$ by image processing. The step VERIF_1 enables a recovery of imaging data IMG by the positioning system SYS_POS. The variations in displacements of tissues may thus be automatically calculated in a region controlled on the recovered position. The computer may be the same as that used for the other calculations of parameters or a computer dedicated to the measurement of tissue deformation. A measurement of the elasticity of the tissue may be deduced from the displacements/deformations of tissues.

Moreover, in FIG. 1, the step VERIF_1 may also refer to a step of monitoring the calibration of the ballistic between the imaging system IMG and the positioning system SYS_POS. This monitoring consists in verifying that the position of a point in space evaluated by one item equipment indeed corresponds to the position of a point in space evaluated by another item of equipment.

According to another embodiment, the temperature and deformation measurements are carried out by different items of equipment. The temperature measurements may, for example, be carried out by an MRI imaging system and the tissue deformation measurements may be carried out by an ultrasound imaging system.

When an imaging system is used, it is possible to visualize tissue deformations ACQ_DEF locally on a 2D section or a 3D slice of the image acquired or instead a region of the 3D image by means of a display AFF_2. The display may be the same as that making it possible to visualise the temperatures of the region of the heart considered or a dedicated display.

Applications/Synchronisation with ECG

Depending on the application, the stimulation by ultrasounds is carried out either during depolarisation of the auricles and/or the ventricles or during repolarisation of the auricles and/or the ventricles.

To carry out this synchronisation, the beam of focussed ultrasound signals $F_{US}$ is synchronised with the rhythm of the ECG of the heart so as to select a time window during which the stimulation is carried out during repolarisation or during depolarisation of the cardiac tissue, depending on the desired physiological effect.

For example, an application of the stimulation during calibration concerns monitoring of the ballistic. Monitoring of the ballistic makes it possible to ensure that the position of the targeted zone indeed corresponds to the position of the focussed zone. Indeed, before the use of the system to carry out a stimulation of a zone of the heart, a calibration of the positions of the different items of equipment enables a gain in precision of the process. Thus, the calibration of the ballistic makes it possible to calibrate the positioning system of the phased array and that which is used for the control, for example an imaging system or a position probe.

In the application which concerns the calibration of the ballistic, the process of the invention makes it possible to generate a stimulation of a focussed zone after the depolarisation of the auricles and/or the ventricles so as not to induce an extrasystole. The calibration process of the invention thus comprises a synchronisation of the phased array with the ECG so as to generate the focussed beam at a precise moment of the cardiac beat.

According to other stimulation applications, such as ventricular or auricular resynchronisation, the phased array is synchronised, at another moment of the cardiac cycle, with the ECG. In this case, the stimulation is carried out after repolarisation of the auricles and/or the ventricles according to the application that it is wished to carry out. The ECG thus makes it possible to synchronise the phased array in order to stimulate, at the desired moment, the cardiac tissue according to the desired physiological effect.

For applications such as the generation of a fibrillation or the generation of an extrasystole, the stimulation is also carried out during the repolarisation of the auricles and/or the ventricles. For the generation of a cardiac fibrillation, the stimulation is advantageously generated during the T-wave of the ECG.

Figure 3:
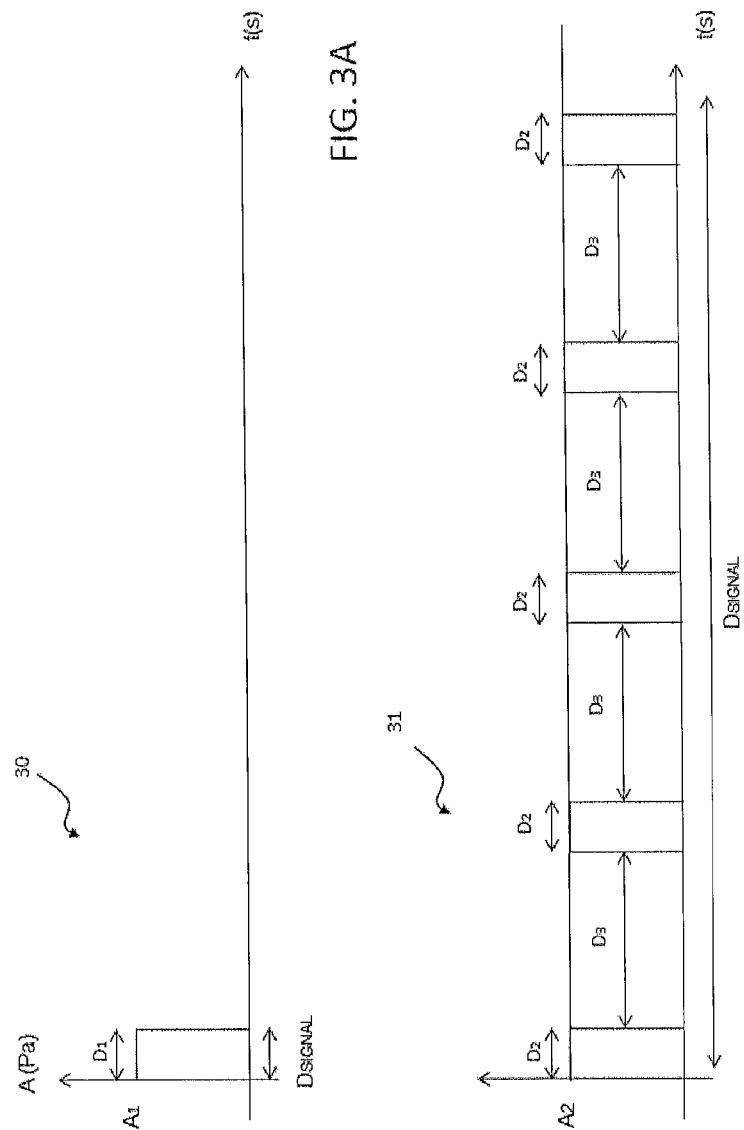
FIG. 3A: a diagram representing the amplitude and the duration of a pulse of a beam of ultrasound signals applied in a targeted zone of the heart for the monitoring of said zone.
FIG. 3B: a diagram representing the amplitude and the duration of a plurality of pulses of a beam of ultrasound signals applied in a targeted zone of the heart for the stimulation of said zone.

FIG. 3A is a diagram representing a pulse, in a targeted zone $Z_C$ of the heart, for monitoring said zone, of a beam of ultrasound signals $F_{US}$ of amplitude $A_1$ and of duration $D_1$, the total application duration being designated $D_{SIGNAL}$. The monitoring process of the invention makes it possible, from a calibration pulse, to define the thresholds of electrical stimulations without causing damage to the tissues.

The amplitudes $A_i$ and the durations $D_i$ of the pulses for the stimulation of the targeted zone $Z_C$ of the heart are chosen so as to minimise preferentially mechanical damage or preferentially thermal damage.

FIG. 3B represents the generation of a focussed beam comprising a succession of pulses in at least one targeted zone $Z_C$ of the heart for the stimulation of said zone. The pulses are applied in a region of the heart controlled on the position of a targeted zone defined beforehand.

The signals of FIG. 3B have an amplitude $A_2$ for a duration $D_2$ and are separated by a time interval $D_i$, the total duration of application being designated $D_{SIGNAL}$. The amplitude of the signal may represent the level of acoustic pressure induced in the focussed zone expressed in Pascals. According to another representation embodiment, the amplitude of the signal $A_2$ may represent the amplitude of the ultrasound beam recomposed in a coherent manner in the focussed zone $Z_F$. The amplitude of the ultrasound beam recomposed in the focussed zone and the acoustic pressure induced by the beam in the focussed zone are linked such that one or the other of these notions may be evoked indifferently to describe the signal of FIG. 3B.

In a first embodiment, the pulses are configured such that the acoustic pressure $A_2$ in the focussed zone $Z_F$ is comprised in a pressure range of [2-8 MPa] for durations of pulses $D_2$ comprised in the duration range [1-50 ms]. The pulses generated are synchronised with the ECG of the patient or the animal. These ranges of values are particularly advantageous to cause an electrical stimulation while maintaining a threshold of mechanical damage to cardiac tissue below a threshold value. Said threshold value is calculated from a parameter corresponding to a given proportion of a contraction or a relaxation or an elasticity of the tissue.

In a second embodiment, the pulses are configured such that the acoustic pressure $A_2$ in the focussed zone $Z_F$ is comprised in a pressure range of [8-12 MPa] for pulse durations $D_2$ comprised in the duration range [50 µs-1 ms].

These ranges of values are particularly advantageous to cause an electrical stimulation while maintaining a threshold of thermal damage of the cardiac tissue below a threshold value, which may be, for example, a temperature threshold value. To do so, a monitoring of the temperature makes it possible to monitor possible thermal damage, which can occur during the generation of the pulses. The temperature measured locally, for example thanks to the MRI, may indicate a risk of thermal damage which can occur.

The pulses are thus generated to cause an electrical stimulation in the cardiac tissues while maintaining locally in the targeted zone ($Z_C$) the temperature below a temperature threshold ($T_{MAX}$).

According to an embodiment, the duration $D_3$ is advantageously longer than 200 ms. According to an embodiment, the duration $D_3$ is advantageously comprised in the QT interval. According to one configuration, a pulse is generated at each cardiac beating cycle. According to other configurations, several cardiac beat cycles may separate the generation of each pulse.

In all the embodiments, active monitoring of zones neighbouring the focussed zone may be carried out by measurement of the electrical activity and/or measurement of tissue deformation and/or measurement of the level of cavitation and/or measurement of the temperature of zones neighbouring the targeted zone $Z_C$ of the heart so as not to damage zones neighbouring the targeted zone $Z_C$.

In all the embodiments, the stimulation method may comprise a monitoring of the ballistic, which may be carried out for example by means of a pulse of the signal and an imaging system. This monitoring during the stimulation method may make it possible to verify that the calibration of the position calibrated during the calibration process is properly maintained. In this case, the monitoring comprises the verification that the focussed zone $Z_F$ and the targeted zone $Z_C$ are merged or substantially close.

FIG. 4 represents diagrams corresponding to the evolution of temperature 40, 41, the deformation of tissue 47, 47' and the phenomenon of cavitation 48 at the level of the targeted zone $Z_C$ of the heart according to the amplitude and the duration of the pulses 42, 43 of a beam of ultrasound signals $F_{US}$ in said zone. Two specific cases are represented according to the envisaged ranges of values defining the focussed beam.

The curves represented are indicative for certain critical points. Conversely, the shapes of the plots are not represented faithfully on the curves obtained during tests.

Tissue deformations 47, 47' and the phenomenon of cavitation 48, 48' are represented in the same graphs 44 and 45.

According to a first specific case, the pulse 42 applied in the targeted zone $Z_C$ of the heart has an amplitude $A_1$ comprised between [2 MPa; 8 MPa] for a duration $D_1$ comprised between [1 ms; 50 ms]. A range of amplitude values of [4 MPa; 8 MPa] makes it possible to obtain a stimulation of the cardiac tissues while considerably limiting the thermally and mechanically destructive effects of the tissues.

At the end of the duration $D_1$, the measured temperature 23 of the targeted zone $Z_C$, noted $T_{mes\_1}$, is close to the maximum temperature $T_{MAX}$ for which cardiac tissue may be damaged by burning. The deformation of cardiac tissue 47 may be observed. Advantageously, the calibration process makes it possible to evaluate the value of the duration $D_1$ of the pulse for which $T_{max}$ is not exceeded.

In this first specific case, in graph 51 of FIGS. 5A and 5B, are represented the probability PROB_DT that thermal damage 52 occurs and the probability PROB_DM that mechanical damage occurs locally to the tissues of the focussed zone as a function of the duration $D_1$ of application of the pulse for a given amplitude $A_1$.

The curve 52 illustrates that the longer the duration $D_1$ of the pulse, the greater the probability of occurrence of thermal damage 52.

A duration threshold, noted $D_{DT}$, is indicated, beyond which the pulse 42 generates heating capable of causing thermal damage. This threshold duration $D_{DT}$ is calculated for a given pulse amplitude. A range of values of durations PD is represented, for which thermal damage 52 is limited.

The same graph represented in FIG. 5B represents the exemplary case during the duration $D_1$ is less than the threshold duration for a given pulse amplitude. In this case, thermal damage is negligible, or even zero.

The duration of application of the pulse may thus be calibrated so as not to exceed a threshold duration for which the increase in local temperature causes thermal damage to the tissues. This local temperature may be measured thanks to an imaging system, such as an MRI. A computer recovering the position of the targeted zone $Z_C$ may extract data from the MRI, such as the local temperature or variations in temperatures in or near to the focussed zone $Z_F$.

A first advantage of the specific case is to be able to monitor thermal damage while generating deformation of the tissues induced by the ultrasound thrust of the beam. The ultrasound thrust on the tissues applied locally may favour the occurrence of a global depolarisation of the ventricle or the auricle obtained by the effect of contraction of the tissues propagating in the organ.

A second advantage of this specific case is to generate a focussed beam of which the amplitude of ultrasonic thrust is less than a threshold in or near to the focussed zone. This threshold is noted in FIGS. 4 and 5: "$A_{destru}$". The threshold $A_{destru}$ corresponds to the amplitude threshold of ultrasound thrust of the focussed beam beyond which mechanical damage occurs on tissues. Mechanical damage is the result of the phenomenon of cavitation favouring the generation of microbubbles locally, which are destroyed under the effect of the thrust; the latter damage tissues during their destruction.

Thus, this first specific case makes it possible to create a focussed beam of which the amplitude of the pulses is managed so as not to cause mechanical damage to the cardiac tissues and the duration of which is also managed so as not to cause thermal damage.

According to a second specific case, the pulse 43 applied in the targeted zone $Z_C$ of the heart has an amplitude $A_1$ comprised between [8 MPa; 12 MPa] for a duration $D_1$ comprised between [50 µs; 1 ms].

At the end of the duration $D_1$, the measured temperature 23' of the targeted zone $Z_C$ $T_{mes\_2}$ is less than a critical temperature threshold notably indicated by the maximum temperature $T_{MAX}$. A case of such a pulse is represented in FIG. 5B. The pulse being of short duration, that is to say less than 1 ms, the tissues have little time to heat up. The stimulation is essentially caused by a phenomenon of cavitation. The deformations of the tissues 47' generated by the ultrasound thrust are small below 1 ms.

This specific case is interesting from the point of view of the absence of thermal damage to tissues, which cannot occur in a duration of pulse less than 1 ms. The part of the curve 52' extending beyond $T_{destru}$ in the zone 59 is represented by considering a pulse 43 which would exceed the duration $D_{DT}$. In this specific case, thermal damage would occur. It may be noted that before $T_{destru}$, the thermal damage 52' of FIGS. 5A and 5B is negligible, or even zero in graph 54.

In this specific case, due to the fact the ultrasound thrust is generated for a very short duration, the viscoelasticity of the tissue does not allow the tissue to generate a mechanical response to the stimulation.

In FIG. 5A, for a higher amplitude in the indicated range, uniquely a phenomenon of cavitation 48' is observed, that is to say a generation of microbubbles exerting a mechanical effect on the cardiac tissues. In FIG. 4, it may be observed that the curve 48, 48' representing the phenomenon of cavitation is dependent on the level of amplitude of the pulse $A1$, $A_1'$. Indeed, the phenomenon of cavitation 48' on the right of FIG. 4 is more important when the amplitude $A_1'$ of the pulse is greater than the amplitude $A_1$, as is represented in FIG. 4 on the left by comparing the curves 48 and 48'.

FIG. 5A represents a curve 55 in the graph 54 representing the probability PROB_DM that mechanical damage occurs during or after the application of a focussed beam when the level of amplitude of the pulse is above a threshold $A_{destru}$. It may be noted that this probability PROB_DM increases with the increase in the amplitude of the focussed beam, as illustrated in curves 55 of FIGS. 5A and 5B. The damage to tissues is essentially linked, in this exemplary case, to a phenomenon of inertial cavitation: the microbubbles explode or vaporise and create lesions in the cardiac tissues. It then involves mechanical damage. The very short period of application of the beam does not enable a rise in the temperature of the tissues in the focussed zone.

There exists a range of amplitudes PA, represented in FIG. 5, of the focussed beam for which the mechanical damage 55 are minimal, or even negligible. A favourable case is represented in FIG. 5B, in which mechanical damage 55 is maintained at very low levels.

A generation of a focussed beam of which the amplitude is less than the amplitude threshold $A_{destru}$ makes it possible to limit mechanical damage linked to the phenomenon of inertial cavitation 42.

In this second specific case, the process of the invention makes it possible to generate so-called "short" pulses of which the amplitude is in a range of values making it possible avoid the destructive phenomenon of inertial cavitation, this phenomenon being able to cause mechanical damage. The short pulses thus have a duration less than a duration beyond which thermal damage to cardiac tissues may occur.

An advantage linked to the second specific case is that the phenomenon of cavitation may lead to a global depolarisation of a ventricle or an auricle when it is applied in one or several targeted zones. This second specific case makes it possible to stimulate the heart electrically without causing damage, for example with a pulse, such as represented on the right side of FIG. 5B. The duration and the amplitude of the pulses are thus monitored and configured so as to define one or more focussed beams for the stimulation of the heart.

In all the embodiments, the measurements of tissue deformation and temperature of the targeted zone $Z_C$ or in its close vicinity may be carried out by a single imaging system. As specified above, according to one embodiment, said imaging system may be an MRI imaging system. According to another embodiment, two different items of equipment, such as for example an MRI imaging system and an ultrasound imaging system, may be combined to determine temperature and deformations in or near to the focussed zone.

The thermal damage which can occur to tissues is, for example, of hyperthermia or coagulation type.

The mechanical damage, when it is induced by the phenomenon of cavitation, may be for example: a volatilisation, a vaporisation or instead a bursting of the bubbles causes lesions in the tissues.

FIG. 6A represents a first focussed beam 50 applied in a targeted zone comprising a train of pulses of duration $D_4$.

According to this embodiment, the amplitude of the pulses $A_4$ is comprised in the range of values [2 MPa; 8 MPa] for a duration $D_4$ comprised in the range of values [1 ms-50 ms] so as to stimulate a targeted zone $Z_C$ while limiting mechanical and thermal damage. The generation of electrical activity, which can induce repolarisation of a ventricle or an auricle, is thus linked to the ultrasound thrust applied to the tissues, which contract.

FIG. 6B represents a second focussed beam 51 applied in a targeted zone comprising a train of pulses of duration $D_4$.

According to this embodiment, the amplitude of the pulses $A_4$ is comprised in the range of values [8 MPa; 12 MPa] for a duration $D_4$ comprised in the range of values [50 µs-1 ms] so as to stimulate a targeted zone $Z_C$ while limiting mechanical and thermal damage. In this case, the generation of electrical activity capable of inducing repolarisation of a ventricle or an auricle is thus linked to the phenomenon of cavitation, of which microbubbles enable the tissues to contract.

According to tests carried out, the following configurations have made it possible to end up with stimulations of tissues of the heart in 90% of cases. In these tests, each stimulation has not caused any thermal or mechanical damage in the focussed zone and/or near to it:

a first configuration making it possible to generate a pressure level in the focussed zone of which the positive amplitude of the acoustic signal is 6 MPa, the corresponding negative amplitude of the acoustic signal being 4 MPa, for a pulse duration of 1 ms. The numerical values of the acoustic pressures and the duration of the pulse can vary by 10% from their nominal value in this example;

a second configuration making it possible to generate a pressure level in the focussed zone of which the positive amplitude of the acoustic signal is 10 MPa, the corresponding negative amplitude of the acoustic signal being 6 MPa, for a pulse duration ranging from 50 µ to 1 ms. The numerical values of the acoustic pressure can vary by 10% from their nominal values in this example.

When an ultrasound contrast agent is used, a reduction in the acoustic pressure thresholds may be obtained by a reduction in the power of the focussed signals in the focussed zone. A reduction of several hundredths of MPa to several MPa may be obtained as a function:

of the mode of administration of the contrast agent;
of its quantity;
of the physiological data of the patient, or instead;
of the period at which the beam is generated after the administration of the contrast agent.

Cardiac Stimulation Applications

The process according to the invention may be used according to various applications requiring cardiac stimulation.

Moreover, the cardiac stimulation method may be applied to purposes other than therapeutic applications. As an example, the cardiac stimulation method may be applied for mapping a region of the heart electrically, by analysing tissue deformations in this region. Another application concerns the analysis of the phenomenon of cavitation in regions of the heart. Other applications are possible.

A first application concerns cardiac resynchronisation. Each pulse of the beam of ultrasound signals is then synchronised with the rhythm of the ECG, each pulse being generated between the end of repolarisation and the start of depolarisation of a ventricle or an auricle.

When it is sought to resynchronise the left and right ventricles, a first embodiment comprises the parameterisation of at least one focussed beam in a targeted zone of a ventricle during repolarisation of the ventricle concerned and taking into account the desynchronisation offset of the two ventricles. Thus, the stimulation may generate electrical activity thereby creating a new QRS complex synchronised between the two ventricles.

A second embodiment comprises the parameterisation of the phased array to at least create a focussed beam in each of the ventricles. In this case, the two beams are generated during repolarisation of the two ventricles but spaced apart by a duration compensating desynchronisation of the ventricles.

The same process of resynchronisation of the auricles may be applied by generating one or several focussed beams during periods of repolarisation of the auricles.

Stimulation of the heart causing resynchronisation of the ventricles or the auricles may be generated by one or more pulses, as defined in one of the two specific cases described in FIGS. 4 to 6B.

The stimulation method of the invention makes it possible to simulate a placement of electrodes or probes fixed to the heart generating pulses to ensure permanent resynchronisation of the ventricles or the auricles. This application is particularly advantageous for the detection of zones of the heart capable of receiving implanted probes which will be fixed to the surface of the heart. The implanted probes serve notably for the detection of a ventricular or auricular desynchronisation to generate pulses from a component also implanted under the skin. An identified problem of current implanted devices is that the probes are sometimes fixed on non-responding zones.

The stimulation method of the invention may thus make it possible to select zones that are reactive to the stimulation before their definitive putting in place.

An application of the process of the invention makes it possible to monitoring the correct working of the heart, for example after cardiac resynchronisation. For this purpose, the imaging system, for example the MRI, makes it possible to measure the improvement in the cardiac function by measuring for example the fraction of blood ejected by the heart.

A second application of the stimulation process concerns the generation of auricular or ventricular fibrillation. Each pulse of the focussed beam is synchronised over a period during which the cardiac tissues are polarised in particular at the moment of generation of the T-wave. The stimulation causing the fibrillation may be generated by one or more pulses, as defined in one of the two specific cases described in FIGS. 4 to 6B.

A third application concerns the detection of one or more particular zones of the heart generating a cardiac arrhythmia. When an arrhythmia is formed, it is possible to locate on the ECG the time at which it appears, this time is noted $T_F$. Each pulse is then synchronised with the identified time $T_F$ determined on the ECG. The stimulation method is then carried out in different zones of the heart. By analysis of the electrical response occurring consequent to the generation of a focussed beam, it is possible to determine whether the targeted zone corresponds to the zone generating the extrasystole. Step by step, by application of different stimulations in different targeted zones, it is possible to identify the zone generating the extrasystole. The analysis of the ECG may reveal a deregulation, making it possible electrically to verify that the stimulated zone causes an arrhythmia. Stimulations enabling the detection of a zone generating an extrasystole may be generated by one or more pulses as defined in one of the two specific cases described in FIGS. 4 to 6B so as to monitor and avert thermal and mechanical damage to the tissues.

A fourth application concerns the detection of one or more electrically non-responding zone(s) of the heart. For example, the stimulation method of the invention may be applied after an ablation of a zone of the heart to verify that the ablated, burned or necrotised part is a non-responding zone or to verify that a non-responding zone is precisely no longer present. An analysis of the electrical response, for example, by means of an electrical catheter makes it possible to deduce electrical activity locally. When the pulse is of a duration above 1 ms, corresponding to the pulses of the first specific case, a correspondence table between the deformation of the tissues and the electrical activity may be used. In this latter case, an electrical catheter is not necessary unless it is used in addition to an imaging making it possible to visualise displacements of the tissues, such as an MRI.

A fifth application concerns that of the modification of the heart beat frequency from at least one cardiac stimulation generated by the process of the invention. This application is also called "pacing" in the medical field.

In this case, the process may be used to increase the frequency of the cardiac rhythm. Each pulse of the beam of ultrasound signals is then emitted at a frequency different to the frequency determined on the ECG so as to synchronise the cardiac rhythm with the pulses of the focussed beam. One of the two specific cases shown in FIGS. 4 to 6B may notably be used by successive pulse trains over given time periods. This application can be a substitute for a cardiac massage.

System-Summary

The invention relates to a system, such as that described in FIG. 1, making it possible to implement the monitoring process for the calibration of a focussed beam or the stimulation method for one of the aforementioned applications. Finally, it should be noted that the system of the invention is modular and may be used in different ways to resolve the problem of controlled stimulation of the invention.

According to a first configuration, an imaging system IMG using an MRI makes it possible to generate an image in 2D or 3D section of the heart. The position of the targeted zone may make it possible to only control the generation of a portion of the image, notably that which concerns the application of the focussed beam. Thus, it is possible to monitor visually the focussed zone on an image slice comprising this zone.

According to one case, the MRI imaging system is configured to determine locally, in or near to the targeted zone, variations in temperatures, this mode is known as MR-T. It may also be configured to determine locally, in or near to the targeted zone, variations in tissue displacements, a mode known as MR-ARFI. The two modes MR-T and MR-ARFI are compatible to be configured in a same application.

According to another case, the temperature monitoring is carried out using an MRI imaging system as previously and the monitoring of tissue deformations is for example carried out by means of a catheter introduced into the heart and measuring local pressure. Tissue deformations may also be deduced from an ultrasound imaging system.

A positioning system may be designed from the definition of a point on the image and by determination of the coordinates in a reference frame of the heart of a targeted position. This position of the targeted zone is then transmitted to the phased arrays RES_US for the generation of a focussed beam, which is thereby controlled dynamically and automatically on this position.

The system comprises, according to an embodiment, a device for measuring a level of cavitation SYS_CAV, for example by means of an ultrasound device as detailed previously.

According to one configuration, the ECG is acquired using electrodes positioned, for example, on a patient. The ECG may also be acquired by any other known means making it possible to reproduce the cardiac frequency.

A single system for acquiring the electrical activity of the heart may be used to determine the ECG and the electrical responses due to the stimulations generated by the process of the invention.

Portable Cardiac Stimulation Device

Figure 7:
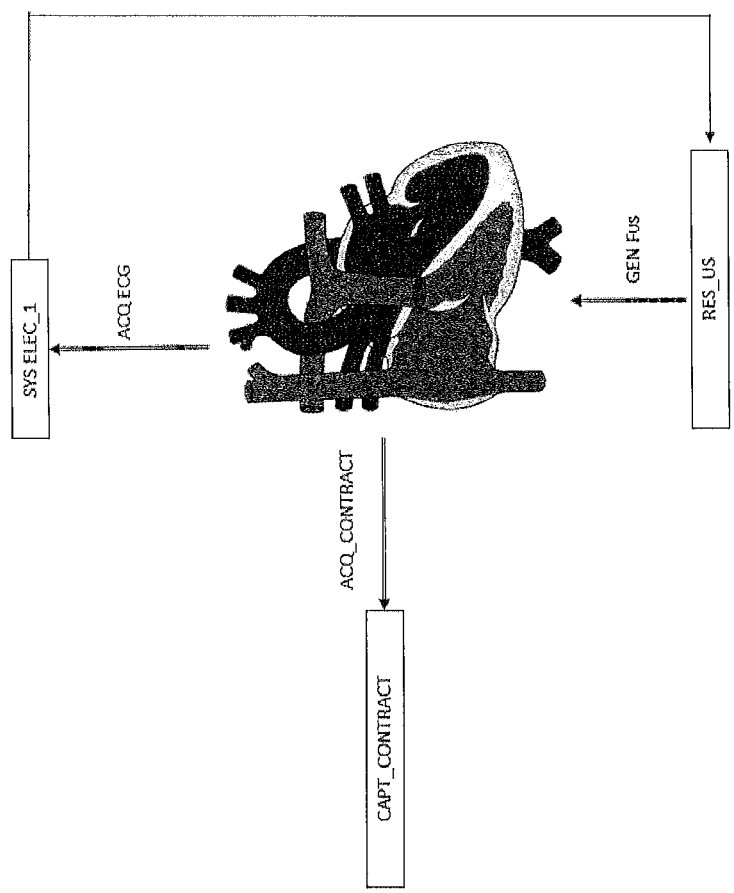
FIG. 7: a portable ultrasound cardiac stimulation device.

Finally a particular mode concerns a portable device comprising predetermined configurations of signals such as those described in the two specific cases shown in FIGS. 4 to 6B. This device is illustrated in FIG. 7. It comprises a generator of ultrasound signals RES_US, which can generate a single signal or a plurality of signals forming a focussed beam. It may be noted that in the case where the beam only comprises a single signal, it is focussed. The beam is preconfigured so as to focus at a certain distance from the emitter. The generator RES_US as in FIG. 1 may be noted, although in this embodiment the generator of ultrasound signals is not necessarily a phased array. According to an embodiment, a plurality of focal distances may define different configurations, for example different distances comprised between 2 and 20 cm.

The device comprises electrical means SYS_ELEC_1 to determine the heart beat frequency at least. According to an improved embodiment, the electrical means SYS_ELEC_1 make it possible to determine a complete ECG.

The device is designed to be affixed to the surface of the skin. Depending on the size of the patient, a focal distance is determined by an operator. The device comprises a means for activating the beam according to a given specific case, the beam generation is synchronised with the cardiac frequency and with the ECG when it is determined. When uniquely the cardiac frequency is used, the moment of repolarisation of the cardiac tissues is calculated from a computer of the device making it possible to evaluate the time window corresponding to repolarisation of the ventricles and/or the auricles. When no cardiac frequency is available, which corresponds to a cardiac arrest, the device does not synchronise with the cardiac frequency or with the ECG and enables the generation of a focussed beam.

According to an embodiment, different pre-configurations of beams are present in the device.

In an exemplary embodiment, a first embodiment exists comprising 3 beam configurations corresponding to the first specific case (so-called long pulses, so-called small amplitudes, corresponding to the specific case 6A).

A first configuration comprises the emission of a pulse, a second configuration comprises the emission of three pulses, a third configuration comprises the emission of 6 pulses.

In a second embodiment comprising 3 beam configurations corresponding to the second specific case (so-called short pulses, so-called large amplitudes, corresponding to the specific case 6B).

A first configuration comprises the emission of one pulse, a second configuration comprises the emission of three pulses, a third configuration comprises the emission of 6 pulses.

The device of the invention further comprises a sensor, making it possible to detect that a mechanical contraction of the heart is present.

As an example, a blood pressure sensor makes it possible to detect that a contraction of the heart has taken place. This sensor may be positioned on the wrist to measure the heart pulse or on the chest to detect the presence of a heartbeat.

Thus, the invention relates to a preconfigured portable device which may be used in emergency situations. It may, for example, be carried on board an emergency services vehicle or be placed in areas in which a cardiac accident may happen to someone.

This on-board device does not necessarily comprise an imaging system when it is wished to limit its bulk. The imaging system may be used during the pre-configuration of signals during the production of the device.

The invention claimed is:

1. A method for calibrating a focussed signal for a stimulation of a targeted zone of a heart, the method comprising:
    acquiring at least one frequency of an electrocardiogram of the heart;
    acquiring at least one image of a region of the heart in which the targeted zone is located, said at least one image being acquired in synchronisation with the at least one frequency acquired from the electrocardiogram of the heart, by a single MRI imaging system;
    generating a first beam of focussed ultrasound signals focussed on the targeted zone, said first beam being emitted by a phased array, said ultrasound signals being configured in phase to generate at least one pulse in a focussed zone within the targeted zone, said at least one pulse being synchronised with the frequency acquired from the electrocardiogram of the heart, the at least one pulse having a predefined amplitude and duration;
    during the generating, performing an active monitoring in real time of a temperature and of a tissue deformation in or near to the focussed zone in response to at least one pulse of the first focussed beam by the single MRI imaging system;
    performing a dynamic control of the phased array as a function of the temperature and tissue deformation monitored by the single MRI imaging system, wherein performing the dynamic control includes dynamic control of a position of the focussed zone on a position of the targeted zone by a positioning system comprising the single MRI imaging system so as to measure displacements of the targeted zone of the heart in a reference frame linked to the phased array, the displacements of the targeted zone being measured by measuring respiratory movements of the heart in the reference frame linked to the phased array using said positioning system and by measuring contraction movements of the heart in the reference frame linked to the phased array using said positioning system and to deduce therefrom a compensation parameter to calculate a new position of the targeted zone and control deflection of the first beam, said phased array automatically applying a phase parameter to each signal to deflect the first beam to the new position of the targeted zone,
    performing an active monitoring in real time of a level of cavitation at a level of the focussed zone by an ultrasound device that detects a spectrum of ultrasound frequencies in or near to the focussed zone, the level of cavitation being deduced from a spectral noise level of the spectrum,
    the amplitude and/or the duration of the at least one pulse being configured such that said cavitation level is less than a first threshold representative of a cavitation damage threshold, and such that said deformation is less than a second threshold representative of a mechanical damage threshold,
    wherein the method further comprises, in a zone of the heart neighbouring the focussed zone:
    measuring a level of cavitation to determine a measured level of cavitation and comparing said measured level of cavitation with the first threshold;

measuring a tissue deformation to determine a measured tissue deformation and comparing the measured tissue deformation with the second threshold, and cutting off the first beam of focussed ultrasound signals when the first threshold, or the second threshold, or both the first and second thresholds, are exceeded.

2. The method according to claim 1, further comprising:
determining by the single MRI an image of a transcostal wall projected in an image plane of the phased array by taking into consideration a position and an orientation of the phased array;

an activation and/or a deactivation of elements of the phased array in accordance with a position of said elements with regard to a position of the projected image of the transcostal wall.

3. The method according to claim 1:
wherein performing the dynamic control includes dynamic control of the deactivation and the activation of the elements of the phased array as a function of a calculation of each phase parameter applied to each of the signals.

4. The method according to claim 1, wherein a comparison of a position of the focussed zone determined by the single Mill imaging system and a position of the targeted zone determined by a positioning system generates at least one data for calibrating elements of the phased array so as to make a position of the focussed zone correspond with the position of the targeted zone.

5. The method according to claim 4, wherein the positioning system is:
either the single Mill imaging system, the position of the focussed zone and the position of the targeted zone being calculated from image processing;
or a positioning system comprising at least one emitter emitting ultrasound waves and a plurality of ultrasound sensors detecting reflected waves, positions being determined by triangulation.

6. The method according to claim 1, further comprising performing in or near to the focussed zone at least one measurement selected from the group consisting of:
a measurement of electrical activity generated by electrical depolarisation induced by application of the at least one pulse; and
a measurement of electrical activity in the focussed zone in response to the at least one pulse.

7. The method according to claim 6, wherein the electrical activity is correlated with measurements of tissue deformations in the targeted zone obtained by the single MRI imaging system, said correlation making it possible to determine an indicator of mechanical-electrical activity of a cardiac tissue of the targeted zone.

8. The method according to claim 1, further comprising performing a calibration of a signal generated in the focussed zone by defining parameters comprising at least one level of the amplitude and duration of a pulse as a function of at least one data selected from the group consisting of:
a temperature set point in the focussed zone and/or in neighbouring zones and/or in ribs of a transcostal wall,
a tissue deformation set point in the focussed zone,
a level of cavitation set point in the focussed zone,
a detection of at least one displacement linked to a movement of the focussed zone in a reference frame linked to the phased array,
an electrical activity set point in the focussed zone, or combinations thereof.

9. The method according to claim 1, further comprising calibrating the focussed signal, the focussed signal comprising a plurality of pulses including the at least one pulse, each pulse of the plurality of pulses having a respective first duration and amplitude, said focussed signal being applied for a duration in the targeted zone.

10. The method according to claim 9, wherein the steps of the method are carried out in different targeted zones of the heart, the method further comprising, after the application of a beam of focussed signals:
a reading of different values representing either tissue deformations of each targeted zone, or electrical levels measured near to or in each targeted zone;
a reading of times of electrical responses or deformations of each targeted zone;
a calibration for each targeted zone of each signal of the beam of focussed signals, each signal of the beam of focussed signals being configured with each other signal of the beam of focussed signals with a time delay dependent on respective readings of the times of electrical responses or deformations of each targeted zone.

11. An ultrasound cardiac stimulation system comprising:
a means for measuring electrical activity of a heart to acquire an electrocardiogram;
a means for generating a beam of focussed ultrasound signals in a targeted zone synchronised with a first selected time of the electrocardiogram, said beam of focussed ultrasound signals being calibrated so as to generate an electrical stimulation in a zone of the heart;
a means for locating the targeted zone, coupled to a means for positioning the means for generating the focussed beam so as to control said beam of focussed ultrasound signals in the targeted zone, said means for locating the targeted zone being synchronised with the means for generating a beam of focussed signals;
a single monitoring means capable of following in real time a temperature and a tissue deformation in the targeted zone, said monitoring means taking measurements in synchronisation with the rhythm of the electrocardiogram and being a single MRI imaging system;
an ultrasound device capable of following a level of cavitation in the targeted zone during a medical procedure, said ultrasound device detecting a spectrum of ultrasound frequencies in the targeted zone in synchronization with the rhythm of the electrocardiogram, the level of cavitation being deduced from a spectral noise level of the spectrum,
a means for performing the dynamic control of the focussed beam as a function of the temperature and tissue deformation monitored by the single MRI imaging system, and of a level of cavitation monitored by the ultrasound device,
wherein the system is configured to implement the steps of the process of claim 1.

12. A method for electrical stimulation of a targeted zone of a heart by generation of a beam of focussed ultrasound pulses, the method comprising:
acquiring at least one frequency of an electrocardiogram of the heart;
determining at least one position of the targeted zone in the heart;
generating the beam by a phased array of focussed ultrasound pulses synchronised with a rhythm of the electrocardiogram of which:
an amplitude of the pulses is configured such that an acoustic pressure applied in the focussed zone is comprised in a first range of pressures of 2-12 MPa;

a duration of the pulses is comprised in a first range of durations of 50 μs-50 ms;
a duration of application of the focussed beam being longer than 50 μs;
controlling a position of a focussed zone of the beam on the position of the targeted zone calculated in real time by a positioning system comprising the single MRI imaging system so as to measure displacements of the targeted zone of the heart in a reference frame linked to the phased array, the displacements of the targeted zone being measured by measuring respiratory movements of the heart in the reference frame linked to the phased array using said positioning system and by measuring contraction movements of the heart in the reference frame linked to the phased array using said positioning system and to deduce therefrom a compensation parameter to calculate a new position of the targeted zone and control deflection of the first beam, said phased array automatically applying a phase parameter to each signal to deflect the first beam to the new position of the targeted zone,
performing an active monitoring in real time in or near to the focussed zone:
of a temperature from an acquisition of image(s) from a single MRI imaging system not exceeding a predetermined threshold and;
of a tissue deformation after each pulse comprised in a predefined range of values from the single MRI imaging system, and of a level of cavitation comprised in a predefined range of values measured after each pulse from an ultrasound device that detects a spectrum of ultrasound frequencies in or near to the focussed zone, the level of cavitation being deduced from a spectral noise level of the spectrum, and/or of an electrical activity comprised in another predefined range of values
of a synchronisation parameter to ensure that the beam of focussed ultrasound pulses is synchronised with the rhythm of the electrocardiogram;
performing a dynamic control of the focused beam as a function and of the cavitation monitored by the ultrasound device and of the temperature and tissue deformation monitored by the single MRI imaging system, to respectively ensure said level of cavitation is less than a first threshold representative of a cavitation damage threshold, and said deformation is less than a second threshold representative of a mechanical damage threshold
wherein the method further comprises, in a zone of the heart neighbouring the focussed zone:
measuring a level of cavitation in or near to the focussed zone to determine a measured level of cavitation and comparing said measured level of cavitation with the first threshold;
measuring a tissue deformation to determine a measured tissue deformation and
comparing the measured tissue deformation with a second threshold, and
cutting off the first beam of focussed ultrasound signals when the first threshold, or the second threshold or both the first and second thresholds are exceeded.

13. A stimulation method according to claim 12, wherein the amplitude of the pulses is configured such that the acoustic pressure applied in the focussed zone is comprised in a second range of pressures of 2-8 MPa for pulse durations comprised in a second range of durations 1 ms-50 ms, said generated pulses causing an electrical stimulation while maintaining the second threshold less than a certain value, said certain value being calculated from a parameter corresponding to a given proportion of a contraction or a relaxation or an elasticity of the tissue.

14. The stimulation method according to claim 12, wherein the amplitude of the pulses is configured such that the acoustic pressure applied in the focussed zone is comprised in a third range of pressures of 6-12 MPa for pulse durations comprised in a third range of durations 50 μs-1 ms, said generated pulses causing an electrical stimulation in the cardiac tissues while maintaining locally in the targeted zone a temperature threshold below a temperature threshold.

15. The stimulation method according to claim 12, wherein an additional monitoring of zones neighbouring the focussed zone is carried out, said additional monitoring including the measurement of an electrical activity in at least one zone neighbouring the focussed zone in response to at least one pulse of the focussed beam.

* * * * *